(12) United States Patent
van der Donk et al.

(10) Patent No.: US 7,985,837 B2
(45) Date of Patent: Jul. 26, 2011

(54) **TWO COMPONENT *BACILLUS* LANTIBIOTIC AND METHODS FOR PRODUCING AND USING THE SAME**

(75) Inventors: Wilfred A. van der Donk, Champaign, IL (US); Lisa E. Cooper, Champaign, IL (US); Amanda L. McClerren, St. Charles, MO (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/931,888

(22) Filed: Oct. 31, 2007

(65) Prior Publication Data

US 2008/0242617 A1 Oct. 2, 2008

Related U.S. Application Data

(63) Continuation-in-part of application No. 11/768,406, filed on Jun. 26, 2007, now abandoned.

(60) Provisional application No. 60/820,646, filed on Jul. 28, 2006.

(51) Int. Cl.
*C07K 1/00* (2006.01)
*C07K 14/00* (2006.01)
*C07K 17/00* (2006.01)

(52) U.S. Cl. .................... 530/350; 424/246.1

(58) Field of Classification Search ............... None
See application file for complete search history.

(56) References Cited

OTHER PUBLICATIONS

Nagao et al Journal of Bioscience and Bioengineering vol. 2 Issue pp. 139-149.*
Bowie et al (Science, 1990, 247:1306-1310).*
Xie et al., "Lactiin 481: In Vitro Reconstitution of Lantibiotic Synthetase Activity", Science 2004 303:679-681.
NCBI Accession No: BAB04173 [gi:10173067] with Revision History, Aug. 3, 2000-May 19, 2007.
NCBI Accession No: BAB04172 [gi:10173066] with Revision History, Aug. 3, 2000-May 19, 2007.
NCBI Accession No: BAB04174 [gi:10173068] with Revision History, Aug. 3, 2000-May 19, 2007.
NCBI Accession No: BAB04171 [gi:10173065] with Revision History, Aug. 3, 2000-May 19, 2007.
NCBI Accession No: AE017333 [gi:52346357] with Revision History, Sep. 29, 2004.

* cited by examiner

*Primary Examiner* — Robert A Zeman
*Assistant Examiner* — Nina Archie
(74) *Attorney, Agent, or Firm* — Licata & Tyrrell P.C.

(57) ABSTRACT

The present invention relates to two-component lantibiotics isolated from *Bacillus* sp. Methods for producing said lantibiotics are provided, wherein dehydration and cyclization of the peptides is carried out by two substrate-specific modifying enzymes. Given the antimicrobial activity of the instant lantibiotics, methods for preventing or treating bacterial infections are also provided.

2 Claims, 4 Drawing Sheets

```
HalA1  MTNLLKEWKMPLERTHNNSNPAGDIFQ-ELEDQDILAGVNGACAWYNISCR-LGNKGAYCTLTVECMPSCN   (SEQ ID NO:3)
HalA2  MVNS-KDLRNPEFRKAQGLQFVDEVNEKELSSLAGSGDVHAQTTWP---CATVGVSVALCP-TTKCTSQC-   (SEQ ID NO:4)
       *.*  :  *:: :  *  : ::  ..: ::  ::   **:   .*: ...*  *
CONC.  M N   K     P  R                EL       V  W      C     G   A C T  C    C
```

FIG. 1A

```
HalA1  MTNLLKEWKMPLERTHNNSNPAGDIFQELEDQDILAGVNGA--CAWYNI-SCRLGNKGAYCTLTVECMPSCN   69  (SEQ ID NO:3)
PlwAa  MK--ISKIEAQAR--KDFFKKIDTNSNLLNVNGA-KCKWWNI-SCDLGNNGHVCTLSHECQVSCN         59  (SEQ ID NO:41)
SacAa  MKSSFLEKDIEEQ--VTWFEEVSEQEFDDDIFGA_STNTFSL-SDYWGNKGNWCTATHECMSWCK         62  (SEQ ID NO:42)
LtnA1  MN----KNEIETQP-VTWLEEVSDQNFDEDVFGA_STNTFSL-SDYWGNNGAWCTLTHECMAWCK         59  (SEQ ID NO:43)
BhtA1  MK-EIQKAGLQEEL-SILMDDAN--NLEQLTAGIGTTVVNSTFSIVLGNKGYICTVTVECMRNCQ         61  (SEQ ID NO:44)
SmbA1  MK-EIQKAGLQEEL-SILMDDAN--NLEQLTAGIGTTVVNSTFSIVLGNKGYICTVTVECMRNCSK        61  (SEQ ID NO:45)
                                        A          B  C
```

FIG. 1B

```
HalA2    MVNSKDLRNPEFRKAQGLQFVDEVNEKELSSLAGSGDVHAQ-TTWPC--ATVGV----     (SEQ ID NO:4)
PlwAb            MTKTSRRKNAIANYLEPVDEKSINESFGAGDPEAR-SGIPC-TIGAAVAA-     (SEQ ID NO:46)
BhtA2        MKSNLLKINNVTEVEKDMVTLIKDEDMELAGG--------STPAC--AIGVVGI-     (SEQ ID NO:47)
SmbA2        MKSNLLKINNVTEMEKNMVTLIKDEDMLAGG---------STPAC--AIGVVGI-     (SEQ ID NO:48)
LtnA2     MKEKNMKKNDTIELQLGKYLEDD-MIELAEGDESHGG---TTPATP-AISILSAYI     (SEQ ID NO:49)
SacAb      MKNELGKFLEENELELGKFSESDMLEITDDEVYAAGTPLALLGGAAT--GVIGYI-     (SEQ ID NO:50)
CylL-AS MLNKENQENYYSNKLELVGPSFEE--LSLEEMEAIQGSGDVQAE-TTPACFTIGLGVGALF   (SEQ ID NO:51)
CytL-AL                     MENLSVVPSFEELSVEEMEAIQGSGDVQAE-TTPVC--AVAATAAA--     (SEQ ID NO:52)

HalA2    SVALC-PTTKCTSQC                 65
PlwAb    SIAVC-PTTKCSKRCGKRKK            67
BhtA2    TVAVTGISTACTSRCINK              62
SmbA2    TVAVTGISTACTSRCINK              61
LtnA2    STNTC-PTTKCTRAC                 65
SacAb    SNQTCP-TTACTRAC                 67
CylL-AS  SAKFC                           63
CytL-AL  SSAACGWVGGGIFTGVTVVVSLKHC       68
```

*FIG. 1C*

```
HalA1    MT-N-LLKEWKMPLERTHNNSNPAGDIFQELEDQD---ILAGVNGACAWYNISCRLGNKGAYCTL
CONC.    ++ WK P+ RT ++ +PAG+I +EL++++    I  G     +S  LGN G  CTX
LanA1    MSKKEMILSWKNPMYRTESSYHPAGNILKELQEEEQHSIAGGTITLSTCAILSKPLGNNGYLCTV

SEQ ID
                                                              NO:
HalA1    TVECMPSCN   (SEQ ID NO:3)                              4
CONC.    T+ECMPSCN   (SEQ ID NO:1)                              2
LanA1    TKECMPSCN   (SEQ ID NO:7)                              8
```

FIG. 2A

```
HalA2    MVNSKDLRNPEFRKAQGL-QFVDEVNEKELSSLAGSGDVHAQTT------WPCATVGVSVA--LCPTTKCTSQC
CONC.         V+E+EL +L G  DV+ +TT          W C T GV+V+      LCPTTKCTS+C
LanA2    VSEEELKALVGGNDVNPETTPATTSSWTCITAGVTVSASLCPTTKCTSRC
```

TWO COMPONENT BACILLUS LANTIBIOTIC AND METHODS FOR PRODUCING AND USING THE SAME

This application is a continuation-in-part application of U.S. patent application Ser. No. 11/768,406, filed Jun. 26, 2007 now abandoned, which claims benefit of priority from U.S. Provisional Patent Application Ser. No. 60/820,646 filed Jul. 28, 2006, the contents of which are incorporated herein by reference in their entireties.

INTRODUCTION

This invention was made in the course of research sponsored by the National Institutes of Health, grant number GM 58822. The government has certain rights in the invention.

BACKGROUND OF THE INVENTION

Antimicrobial peptides are produced by a wide variety of organisms including bacteria, insects, and mammals (Hancock (1998) *Expert Opin. Investig. Drugs* 7:167-74; Jack & Jung (2000) *Curr. Opin. Chem. Biol.* 4:310-7; Toke (2005) *Biopolymers* 80:717-735). Due to the rapid spread of multiple-drug resistant bacterial strains, antimicrobial peptides are currently being investigated as a potential new source of antibiotics to treat infections. Antimicrobial peptides have a high degree of structural and chemical diversity, exhibit rapid bactericidal action, and typically display a broad spectrum of activity. The lantibiotic group of bacterial-derived antimicrobial peptides possesses high antibacterial activity against Gram positive bacteria including drug resistant strains (Delves-Broughton, et al. (1996) *Antonie vanLeeuwenhoek* 69:193-202; Kruszewska, et al. (2004) *J. Antimicrob. Chemother.* 54:648-53; Brumfitt, et al. (2002) *J. Antimicrob. Chemother.* 50:731-4; Galvin, et al. (1999) *Lett. Appl. Microbiol.* 28:355-8; Goldstein, et al. (1998) *J. Antimicrob. Chemother.* 42:277-8; Cotter, et al. (2005) *Nat. Rev. Microbiol.* 3:777-88). Over 45 members have been identified in the lantibiotic family (Chatterjee, et al. (2005) *Chem. Rev.* 105: 633-84). The most studied lantibiotic, nisin, is produced by *Lactococcus lactis* and has been used world-wide in food preservation for over 40 years (Delves-Broughton, et al. (1996) supra; Hurst (1981) *Adv. Appl. Microbiol.* 27:85-123; Rayman, et al. (1981) *Appl. Environ. Microbiol.* 41:375-80). Lantibiotics share the presence of lanthionine (Lan) and/or methyllanthionine (MeLan) residues, and also typically the unsaturated amino acids dehydroalanine (Dha) and dehydrobutyrine (Dhb). These structural motifs are the basis for their biological activity as well as their family name (Schnell, et al. (1988) *Nature* 333:276-278).

Lantibiotics are ribosomally synthesized as precursor peptides (prepeptides) that are subjected to post-translational modifications to produce the active, mature compounds (Cotter, et al. (2005) *Nat. Rev. Microbiol.* 3:777-88; Chatterjee, et al. (2005) *Chem. Rev.* 105:633-84). The prepeptide contains an amino-terminal leader sequence that does not undergo post-translational modification. The role of this leader sequence appears to be required for modification of the structural region and must be removed by proteolysis in the final step to produce the mature lantibiotic (Schnell, et al. (1988) *Nature* 333:276-278; van der Meer, et al. (1994) *J. Biol. Chem.* 269:3555-62; Xie, et al. (2004) *Science* 303:679-81; Li, et al. (2006) *Science* 5766:1464-7). The dehydro amino acids (Dha and Dhb) found in lantibiotics are introduced via the dehydration of serine and threonine residues located in the carboxy-terminal structural region of the prepeptide. Lanthionine (Lan) and methyllanthionine (MeLan) rings can then be generated by intramolecular conjugate additions of cysteine residues to these $\alpha,\beta$-unsaturated amino acids.

A growing class of two-component lantibiotic systems utilizes two peptides that are each post-translationally modified to an active form and act in synergy to provide antibacterial activity (Garneau, et al. (2002) *Biochimie* 84:577-92). Dehydration and cyclization of the prepeptides to form lanthionine bridges in these systems is likely performed by bifunctional LanM proteins. In most cases the sequence similarity of the two peptides is rather low (~25%), and so two different enzymes are thought to be employed for the post-translational modification of each peptide (McAuliffe, et al. (2000) *Microbiology* 146:2147-54). The exception is cytolysin, a two-component lantibiotic that is processed by a single LanM enzyme (Cox, et al. (2005) *Curr. Protein Pept. Sci.* 6:77-84). In this case, the sequence homology of the two peptide substrates is much higher at ~90%. Other post-translational modifications of the peptides in two-component systems can include the conversion of L-Ser to D-Ala (Skaugen, et al. (1994) *J. Biol. Chem.* 269:27183-27185; Cotter, et al. (2005) *Proc. Natl. Acad. Sci.* USA 102:18584-9) and formation of amino-terminal α-keto amides from the deamination of dehydro residues (Martin, et al. (2004) *Biochemistry* 43:3049-3056).

The best-studied two-component lantibiotic, lacticin 3147, is composed of the modified peptides LtnA1 and LtnA2, and is produced by *Lactococcus lactis* (Ryan, et al. (1999) *J. Biol. Chem.* 274:37544-50). Since the designation LtnA1 and LtnA2 also refers to the unmodified prepeptides, the designations Ltn1 and Ltn2 are used herein for the mature, active components. The post-translational modification of each prepeptide is believed to be catalyzed by two separate bifunctional enzymes, LtnM1 and LtnM2, based on genetic data in which deletion of either LanM gene results in abrogation of bioactive material (McAuliffe, et al. (2000) supra). To date, in vitro activity of LtnM1 or LtnM2 has not been demonstrated. The Ltn1 and Ltn2 peptides act in synergy in a 1:1 ratio to produce nanomolar antibacterial activity (Morgan, et al. (2005) *Antimicrob. Agents Chemother.* 49:2606-11). A study on the mode of action of lacticin 3147 demonstrated that Ltn1 binds to the peptidoglycan precursor lipid II (Wiedemann, et al. (Jun. 12, 2006) *Mol. Microbiol.*), a result that was anticipated because of the structural similarity between Ltn1 and mersacidin, which also disrupts cell wall biosynthesis by binding to lipid II (Brötz, et al. (1998) *Mol. Microbiol.* 30:317-327). In order for lacticin 3147 to substantially inhibit cell wall biosynthesis and form small pores in the cell membrane, however, Ltn2 is also necessary, leading to a proposed model in which the lipid II:Ltn1 complex recruits Ltn2 to form a high affinity complex (Wiedemann, et al. (Jun. 12, 2006) supra). Structural characterization of the modified peptides has indicated that Ltn1 adopts a globular conformation similar to mersacidin, while Ltn2 has a more elongated structure that is α-helical in nature (Martin, et al. (2004) supra).

The mechanisms governing substrate recognition and specificity in two-component lantibiotic systems that utilize two modification enzymes are of great interest since it is believed that each LanM protein is required to discriminate between the two prepeptides present in the cell. Needed in the art is a method for in vitro reconstitution of a two-component lantibiotic biosynthetic system to provide definitive support for the roles of the proteins involved and demonstrate recognition and specificity. Such a system could be used to develop novel lantibiotics based on designing peptide sequences that can be site-specifically modified to yield new products. Given the synergy observed among two-component lantibiotics, which display similar or higher activity than the best single-component lantibiotic nisin (Morgan, et al. (2005) supra), the engineering of new lantibiotics with therapeutic potential could be realized.

SUMMARY OF THE INVENTION

The present invention is a two-component *Bacillus* lantibiotic composed of the amino acid sequences set forth in SEQ ID NO:1 and SEQ ID NO:2. Pharmaceutical compositions containing said lantibiotic, as well as nucleic acid molecules, vectors, and host cells expressing said lantibiotic are also provided.

The present invention is also a method for producing the two-component *Bacillus* lantibiotic of the present invention. The method involves contacting precursor peptides containing amino acids sequences set forth in SEQ ID NO:1 and SEQ ID NO:2 with at least one modifying enzyme capable of effecting dehydration and cyclization of the precursor peptide, and cleaving the leader peptide from the precursor peptides thereby producing a biologically active two-component *Bacillus* lantibiotic.

The present invention further relates to a *Bacillus* lantibiotic modifying enzyme which effects dehydration and cyclization of a peptide or polypeptide and a method for using the same to modify a peptide or polypeptide. Nucleic acid molecules, vectors, and host cells expressing said lantibiotic modifying enzymes are also provided.

The present invention is also a kit for producing haloduracin, wherein said kit contains precursor peptides HalA1 and HalA2 and modifying enzymes HalM1 and HalM2.

Methods for preventing or inhibiting the growth of a bacterium and preventing or treating a bacterial infection using an effective amount of the two-component *Bacillus* lantibiotic of the present invention are also provided.

BRIEF DESCRIPTION OF THE DRAWINGS

FIGS. 1A-1C show the sequence alignments of HalA1 and HalA2 (FIG. 1A); HalA1 with the α prepeptides from plantaracin W (PlwAα), staphylococcin C55 (SacAα), lacticin 3147 (LtnA1), BhtA1, and SmbA1 (FIG. 1B); and of HalA2 with the β prepeptides from plantaracin W (PlwAβ), lacticin 3147 (LtnA2), BhtA2, SmbA2, SacAβ, and the two peptides of cytolysin (CylL-AS and CylL-AL)(FIG. 1C). Serine and threonine residues in the structural regions are underlined, as are the cysteine residues that may be involved in lanthionine thioether formation. The conserved protease cleavage sequences are boxed.

FIG. 2 shows the amino acid sequence of HalA1 (FIG. 2A) or HalA2 (FIG. 2B) from *B. halodurans* aligned with the amino acid sequence of the lantibiotic alpha (FIG. 2A) or beta (FIG. 2B) peptide from *B. licheniformis*.

DETAILED DESCRIPTION OF THE INVENTION

Figure 3:
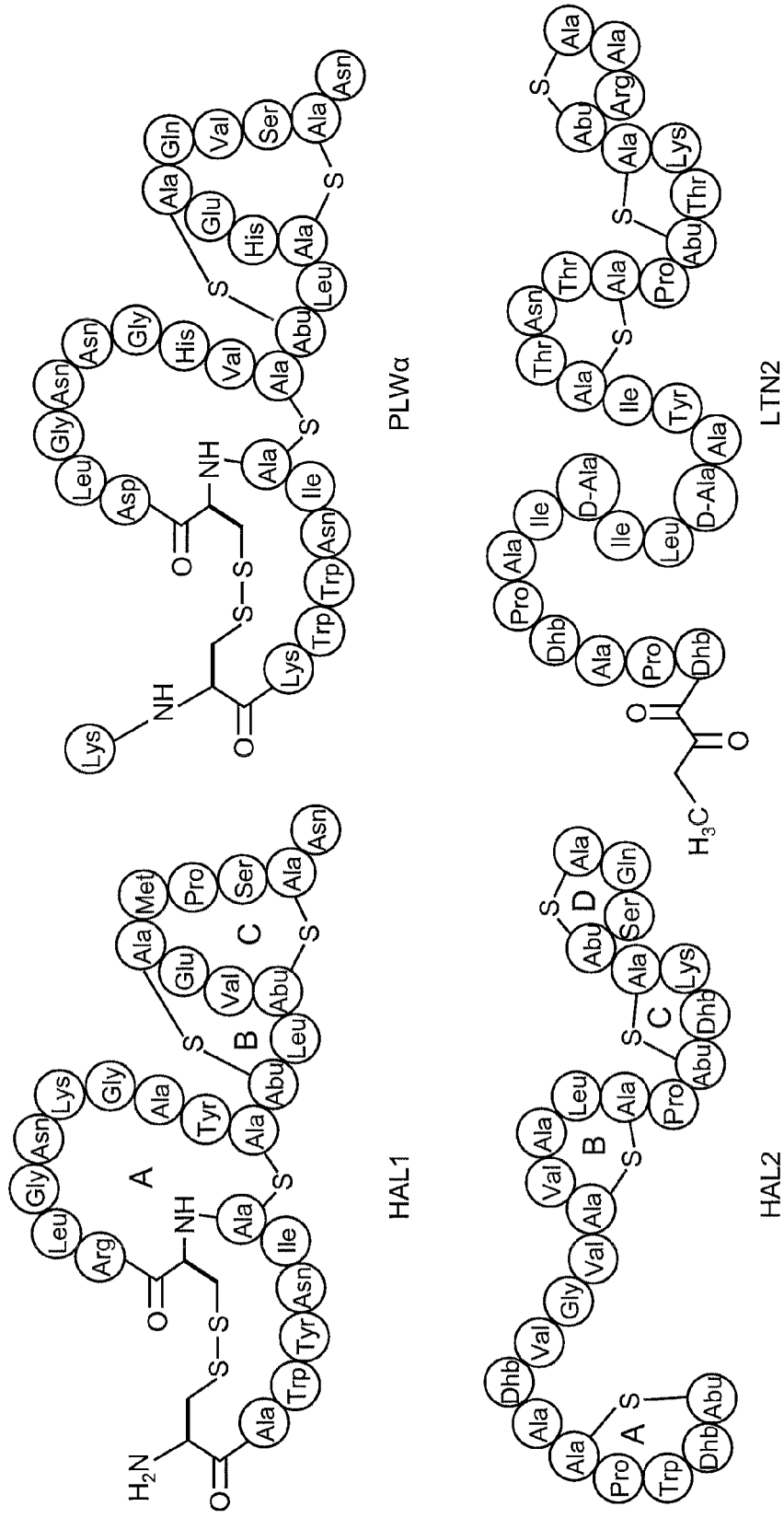
FIG. 3 shows the proposed structures for the Hal1 (SEQ ID NO:5) and Hal2 (SEQ ID NO:6) peptides of the two-component lantibiotic haloduracin. The closest structural analogs, the alpha peptide from plantaricin, Plwα (SEQ ID NO:53), and the Ltn2 peptide (SEQ ID NO:54) from lacticin 3147, are shown for comparison. Dehydrobutyrine (Dhb) and Dehydroalanine (Dha) residues are indicated. MeLan and Lan bridges are indicated as are cystine linkages. Rings in Hal peptides are indicated by letters to correspond to discussion in the Examples.

Lantibiotics are ribosomally synthesized peptides that undergo post-translational modifications to their mature, antimicrobial form. They are characterized by the presence of the unique amino acid lanthionine, which is introduced via dehydration of Ser/Thr residues followed by reaction of the resulting dehydro amino acids with cysteines to form thioether linkages. Two-component lantibiotics utilize two peptides that are each post-translationally modified to yield two functionally distinct products that act in synergy to provide bactericidal activity. For the purposes of the present invention, the term peptide is intended to embrace a string of amino acid residues of 100 amino acids in length, wherein the term polypeptide or protein generally refers to molecules of greater than 100 amino acids in length.

Novel two-component lantibiotics from *Bacillus* sp. have now been identified. Haloduracin, encoded by the genome of the Gram-positive alkaliphilic bacterium *Bacillus halodurans* C-125, was heterologously expressed and the purified precursor peptides, HalA1 and HalA2, were processed by the expressed and purified modification enzymes HalM1 and HalM2 in an in vitro reconstitution assay. The activity of each HalM enzyme was substrate-specific and the assay products exhibited antimicrobial activity after removal of their leader sequences at an engineered Factor Xa cleavage site, indicating that correct thioether formation had occurred. Haloduracin's biological activity was dependent on the presence of both modified peptides and was comparable to the bactericidal effects exhibited by the peptides isolated from the producer strain. The structures of the two mature haloduracin peptides, Hal1 and Hal2, were determined and have similarities as well as some distinct differences compared to other known two-component lantibiotics.

Moreover, HalA1 and HalA2 exhibit sequence identity (39.2% and 35.6%, respectively) with lantibiotic alpha and beta peptides encoded by *Bacillus licheniformis*. Similar to the haloduracin gene cluster, *B. licheniformis* encodes two prepeptides, two modification enzymes, and several additional transport, immunity, and regulation proteins involved in lantibiotic biosynthesis. Of significance is the nearly identical C-termini of the mature *B. halodurans* and *B. licheniformis* lantibiotic peptides. Wherein the alpha peptides share the common amino acid sequence Cys-Thr-Xaa$_1$-Thr-Xaa$_2$-Glu-Cys-Met-Pro-Ser-Cys-Asn (SEQ ID NO:1), wherein Xaa$_1$ is an aliphatic amino acid residue (e.g., Ile, Val, or Leu) and Xaa$_2$ is any amino acid residue; the beta peptides share the common amino acid sequence Leu-Cys-Pro-Thr-Thr-Lys-Cys-Thr-Ser-Xaa$_1$-Cys (SEQ ID NO:2), wherein Xaa$_1$ is Gln or Arg.

Accordingly, the present invention is a two-component *Bacillus* lantibiotic composed of alpha and beta peptides comprising the amino acid sequences set forth in SEQ ID NO:1 and SEQ ID NO:2, respectively. As used herein, the term "lantibiotic" refers to a biologically active compound that acts so as to modify the ability of a target organism to develop, grow, proliferate, or otherwise function. The term can optionally include a compound derived by genetic engineering techniques, synthetic techniques, or a combination of techniques. For example, a lantibiotic can be at least partially synthetic and at least partially recombinant; thus the term can include variants of natural lantibiotics.

The term "target organism" refers to bacteria, viruses, fungi, or protozoa. Target organisms can also include a mammal, particularly a human. In the case of a multicellular organism such as a human, the term is meant to broadly convey a cell, tissue, organ, or fluid of the organism, whether in vivo, ex vivo, or in vitro. In a particular embodiment, the target organism is a bacterium and the compound acts to reduce or control growth or proliferation of the bacterium.

Two-component *Bacillus* lantibiotics include the haloduracin alpha and beta peptides isolated from *B. halodurans*, as well as the alpha and beta peptides of the lantibiotic isolated from *B. licheniformis*. In one embodiment, the present invention provides the *B. halodurans* alpha and beta haloduracin prepeptides (i.e., HalA1 and HalA2) set forth as SEQ ID NO:3 and SEQ ID NO:4, respectively. In another embodiment, the present invention provides the mature *B. halodurans* alpha and beta haloduracin peptides (i.e., Hal1 and Hal2) set forth as SEQ ID NOs:5 and 6, respectively. The haloduracin alpha peptide is composed of 28 amino acid residues in its mature form and has a molecular weight of 2332 Da, whereas the beta peptide is first processed to a 30 amino acid residue peptide which is subsequently further cleaved to 24 amino acid residues in its mature form having a molecular weight of 3046 Da. In yet another embodiment, the present invention provides the *B. licheniformis* alpha and beta lantibiotic prepeptides set forth as SEQ ID NOs:7 and 8, respectively. In still another embodiment, the present invention provides *Bacillus* alpha and beta peptides containing an exogenous protease cleavage sequence such as that recognized by Factor Xa, i.e., Ile-Glu-Gly-Arg (SEQ ID NO:9). Exemplary haloduracin alpha and beta peptide amino acid sequences containing an exogenous protease cleavage sequence are set forth herein as SEQ ID NO:10 and SEQ ID NO:11, respectively. Moreover, it is contemplated that the lantibiotic subunits are interchangeable, e.g., an alpha subunit of haloduracin can be combined with a beta subunit of the *B. licheniformis* lantibiotic to produce a biologically active lantibiotic.

The two-component *Bacillus* lantibiotics of the present invention can be isolated and purified from the respective *Bacillus* species which naturally produce the desired lantibiotic using methods as exemplified herein or well-known in the art of lantibiotic purification; expressed in a heterologous system (e.g., *E. coli*) via the nucleic acid molecules disclosed herein; produced via in vitro translation, or chemically synthesized using established methods. As used herein, the term "purified" refers to a molecule having been separated from a cellular component.

Whether produced in vitro, in vivo or chemically synthesized, the instant lantibiotic peptides can be composed of natural, non-proteinogenic, unnatural or derivatized amino acid residues. In the context of the present invention, a natural amino acid includes one of the 20 naturally occurring amino acid residues (i.e., alanine, arginine, asparagine, aspartic acid, cysteine, glutamic acid, glutamine, glycine, histidine, isoleucine, leucine, lysine, methionine, phenylalanine, praline, serine, threonine, tryptophan, tyrosine, valine), whereas the term "derivatized amino acid" refers to any amino acid that is derivatized chemically or biosynthetically. An example of a derivatized amino acid is selenocysteine. Further, the term "non-proteinogenic amino acid" as used in the context of the present invention refers to an amino acid that is not incorporated by normal in vivo biosynthesis into a protein and "unnatural amino acid" refers to a synthetic amino acid or refers to an amino acid that is typically foreign to a particular organism. Unnatural amino acids can optionally be a subset of non-proteinogenic amino acids.

By way of illustration, a synthetic biologically active lantibiotic containing at least one non-proteinogenic amino acid, unnatural amino acid, peptoid, beta amino acid, or derivatized amino acid can be produced by generating a first precursor lantibiotic peptide; generating a second precursor lantibiotic peptide, wherein said second precursor lantibiotic peptide contains at least one unnatural amino acid, peptoid, or derivatized amino acid; and combining said first and second precursor lantibiotic peptides so as to produce a third precursor lantibiotic peptide which contains the at least one unnatural amino acid, peptoid, or derivatized amino acid. In such an approach, the step of combining the precursor peptides can include ligation, conjugation, or other connection of said first precursor peptide to said second precursor peptide. A synthetic biologically active lantibiotic thus produced can be further reacted with an effective amount of a purified modifying enzyme as disclosed herein to effect dehydration and cyclization of the third precursor peptide. The leader peptide of the precursor lantibiotic peptide can than be cleaved using a suitable protease.

In this regard, it has been demonstrated that His6-LctA(1-38) and His6-LctA(1-38)Cys38Sec can be produced by expressed protein ligation (EPL) (Reis, et al. (1994). *Appl. Environ. Microbiol.* 60:2876-83) of the His6-LctA(1-37)-intein-CBD fusion with cysteine and selenocysteine (Sec), respectively. See U.S. patent application Ser. No. 11/034,275. Thus, it is contemplated that like LctM, semisynthetic *Bacillus* lantibiotic peptide substrates generated by EPL will be recognized by HalM1 and HalM2 for lantibiotic engineering of haloduracin as well as other lantibiotics including subtilin and nisin.

Given the substrate promiscuity of lantibiotic modifying enzymes such as LctM, it is contemplated that HalM1 and HalM2 can also be used in the production of novel lantibiotics. To demonstrate this, steric and electronic tolerance of the enzymes is assessed. This is followed by the incorporation of amino acids designed to answer specific questions about the post-translational modification process including mutants that incorporate peptide fragments from other lantibiotic prepeptides. The structural diversity accessible by these studies is greatly increased by using semi-synthetic substrates prepared by combinatorial parallel synthesis. In addition to the fundamental scientific knowledge that comes forth from these studies, they allow access to molecules with interesting properties that are not easily prepared by either chemical or biological techniques.

Thus, the present invention also relates to isolated and purified nucleotide sequences encoding the *Bacillus* lantibiotics disclosed herein. In one embodiment, the present invention provides the nucleic acid molecules set forth in SEQ ID NOs:12 and 13 which encode the *B. halodurans* alpha and beta haloduracin prepeptides (i.e., HalA1 and HalA2), respectively. In another embodiment, the present invention embraces nucleic acid molecules which encode alpha and beta subunits of the *B. licheniformis* two-component lantibiotic (i.e., SEQ ID NOs:14 and 15) In another embodiment, the present invention provides for nucleic acid molecules encoding lantibiotic modifying enzymes. Exemplary HalM1 and HalM2 nucleic acid molecules are set forth in SEQ ID NOs: 16 and 17, whereas exemplary nucleic acid molecules encoding LanM1 and LanM2 are set forth in SEQ ID NOs:18 and 19).

Modifications to the nucleic acids of the present invention are also contemplated as long as the essential structure and function of the peptide or polypeptide encoded by the nucleic acids are maintained. Likewise, fragments used as primers or probes can have substitutions as long as enough complementary bases exist for selective, specific hybridization with high stringency.

Modifications of the peptides or polypeptides specifically disclosed herein, include amino acid substitutions based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are employed.

In making amino acid substitutions, the hydropathic index of amino acids can be considered. The importance of the hydropathic amino acid index in conferring interactive biologic function on a protein is generally understood in the art (see, Kyte and Doolittle (1982) *J. Mol. Biol.* 157:105). It is accepted that the relative hydropathic character of the amino acid contributes to the secondary structure of the resultant protein, which in turn defines the interaction of the protein with other molecules.

Polymorphisms are also embraced by the present invention. Polymorphisms are variants in the gene sequence. They can be sequence shifts found between various bacterial strains and isolates which, while having a different sequence, produce functionally equivalent gene products. Polymorphisms also encompass variations which can be classified as alleles and/or mutations which can produce gene products which may have an altered function. Polymorphisms also encompass variations which can be classified as alleles and/or mutations which either produce no gene product, an inactive gene product, or increased levels of gene product.

As exemplified herein, nucleic acid molecules of the present invention can be expressed separately, i.e., inserted into separate vectors for expression and purification of individual gene products, namely alpha and beta peptides and modifying enzymes, or alternatively collectively (e.g., as a gene cluster) inserted into a vector as an expression cassette. The nucleic acid molecules of the invention can encode for alpha and beta peptides and modifying enzymes as well as fusion proteins thereof. Fusion proteins include fusions with a heterologous polypeptide or peptide, i.e. a signal sequence for secretion and/or other polypeptide which will aid in the purification of peptide or polypeptide (e.g., GST, His6, or the like). Such vectors are known or can be constructed by those skilled in the art and generally contain all expression elements (e.g., promoters, terminator fragments, enhancer elements, marker genes and other elements as appropriate) necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses, and retroviruses, DNA viruses, cosmids, plasmids, and other recombination vectors. The vectors can also contain elements for use in either prokaryotic or eukaryotic host systems. One of ordinary skill in the art will know which host systems are compatible with a particular vector.

The vectors can be introduced into cells or tissues and expressed by any one of a variety of known methods within the art. Such methods can be found generally described in Sambrook et al. (1989, 1992) *Molecular Cloning: A Laboratory Manual*, Cold Springs Harbor Laboratory, New York; Ausubel et al. (1989) Current Protocols in Molecular *Biology*, John Wiley and Sons, Baltimore, Md.; Chang, et al. (1995) *Somatic Gene Therapy*, CRC Press, Ann Arbor, Mich.; Vega, et al. (1995) *Gene Targeting*, CRC Press, Ann Arbor, Mich.; *Vectors: A Survey of Molecular Cloning Vectors and Their Uses*, Butterworths, Boston, Mass. (1988); and include, for example, stable or transient transfection, lipofection, electroporation and infection with recombinant viral vectors. Introduction of nucleic acids by infection offers several advantages over other listed methods. Higher efficiencies can be obtained due to their infectious nature. Moreover, viruses are very specialized and typically infect and propagate in specific cell types. Thus, their natural specificity can be used to target the vectors to specific cell types in vivo or within a tissue or mixed culture of cells. The viral vectors can also be modified with specific receptors or ligands to alter target specificity through receptor mediated events.

Host cells suitable for introduction and expression of the nucleic acids of the invention are desirably bacterial; however, yeast (e.g., *Pichia, Saccharomyces*, etc.), mammalian, or insect host cells are also contemplated as is a cell-free expression system. In particular embodiments, the host cell or culture is bacterial. Exemplary bacterial host cells include *E. coli* as well as *Bacillus* sp.

As will be understood by the skilled artisan upon reading the instant disclosure, precursor lantibiotic peptides are generally first modified and then become biologically active (i.e., they prevent or inhibit the growth of a target organism) by proteolytic cleavage of the leader peptide from the mature peptide; wherein cleavage can occur prior to, concomitantly with or after export from the cell. Therefore, the alpha and beta lantibiotic precursor peptides can be expressed or synthesized with an endogenous protease cleavage sequence; or expressed or synthesized with an exogenous protease cleavage sequence which can be cleaved by a selected protease, e.g., Factor Xa, thereby effecting removal of the leader peptide. In this regard, the instant lantibiotic precursor peptides can proteolytically processed in vivo or processed in vitro under controlled conditions. Alternatively, the mature form of the peptides can be directly expressed or synthesized. As such, in one embodiment, an intact leader or structural peptide is not essential. For example, it is contemplated that the leader peptide can be combined with the mature form of the lantibiotic peptide in trans to facilitate the dehydration and cyclization of the mature peptide by a modifying enzyme.

Likewise, enzymes that modify the instant lantibiotic peptides (e.g., HalM1 and HalM2 or LanM1 and LanM2) can be co-expressed by a recombinant host cell which expresses the alpha and beta peptides to provide in vivo modification of the peptides, or alternatively the modifying enzymes can be provided in an in vitro reconstitution reaction to modify the alpha and beta peptides. Accordingly, contact of a lantibiotic peptide with a modifying enzyme specifically encompasses both in vivo and in vitro embodiments.

A *Bacillus* lantibiotic modifying enzyme of the present invention refers to a polypeptide or fragment thereof capable of acting upon an alpha or beta lantibiotic peptide so as to effect both at least one dehydration reaction and at least one cyclization reaction. In this regard, the present invention also provides a purified modifying enzyme capable of producing a biologically active lantibiotic peptide by effecting dehydration and cyclization of a precursor peptide. In one embodiment, the *Bacillus* lantibiotic modifying enzyme is a HalM1 enzyme. In another embodiment, the *Bacillus* lantibiotic modifying enzyme is a HalM2 enzyme. In particular embodiments, the *Bacillus* lantibiotic modifying enzyme is HalM1 or HalM2 having an amino acid sequence as respectively set forth in SEQ ID NOs:20 and 21. In other embodiments, *Bacillus* lantibiotic modifying enzymes are obtained from *B. licheniformis* (i.e., LanM1 and LanM2), the amino acid sequence of which are set forth herein as SEQ ID Nos:22 and 23, respectively. Still other embodiments contemplate the use of CinM (cinnamycin LanM), MrsM (mersacidin LanM), MutM (mutacin II LanM), ScnM (streptococcin A-FF22 LanM), RumM (ruminococcin A LanM), LtnM1 and LtnM2 (lacticin 3147 LanM), LctM (lacticin 481 LanM), or NukM modifying enzymes to effect dehydration and cyclization of the instant two-component *Bacillus* lantibiotics.

As has been demonstrated (Sahl and Bierbaum (1998) *Annu. Rev. Microbiol.* 52:41-79), the proteins which are involved in post-translational processing and modification of lantibiotics can be used in vitro to modify other polypeptides or peptides (especially other lantibiotics) and increase the stability of such molecules. As such, particular embodiments embrace the use of a *Bacillus* HalM1 or HalM2 enzyme or a LanM1 or LanM2 enzyme to modify HalA1 or HalA2 (i.e., haloduracin) peptides; or LanA1 or LanA2 peptides as well as other polypeptides and lantibiotics. By way of illustration, such a method involves contacting a primary translation product of another lantibiotics (e.g., duramycin) with a modifying enzyme of the invention so that the modifying enzyme effects dehydration and cyclization of the lantibiotic. Such a method can be carried our in vitro, using the translation products, or in vivo, e.g., by introducing the structural gene for another lantibiotic into a host cell which expresses HalM1 or HalM2 enzyme or LanM1 or LanM2 enzyme.

Having demonstrated in vitro reconstitution of HalM1 and HalM2 for producing haloduracin, the present invention also relates to a kit containing precursor peptides HalA1 and HalA2 in combination with modifying enzymes HalM1 and HalM2 for producing haloduracin. Alternatively, the kit can contain *B. licheniformis* alpha and beta peptides in combination with LanM1 and LanM2 modifying enzymes. The kit can further contain buffers suitable for carrying out dehydration and cyclization of the precursor peptides and an instruction manual. In some embodiments, the alpha and beta precursor peptides contain exogenous protease cleavage sequences and the kit further contains a selected protease which recognizes and cleaves the exogenous protease cleavage sequence.

Using the in vitro biosynthesis system disclosed herein, antimicrobial peptide design and engineering is now possible. The in vitro biosynthesis system allows detailed investigation of the substrate specificity of each individual modifying enzyme as site-directed mutants are readily and rapidly accessible through combinatorial methods. Evaluation of substrate specificity in vitro has advantages over in vivo methods for a complex system like lantibiotic biosynthesis. In particular, when a lantibiotic producing strain shows low or no bioactivity after mutation of the substrate peptide, this can imply the original residue was critical for biological activity, or alternatively it may be due to failure of the biosynthetic proteins (dehydratase, cyclase, or protease), poor expression of the mutant substrates, inability of the wild-type transport proteins to secrete the processed mutants, breakdown of the analog products, or potential toxicity of the non-natural products to the producing strain due to non-recognition of the mutants by the innate immunity proteins. As such, substrate specificity of the biosynthetic proteins can be examined in a much more controlled fashion, and improved lantibiotic variants thus identified can be invaluable starting points to subsequently engineer and optimize an in vivo production system.

In particular, it is contemplated that non-silent mutations of the alpha or beta lantibiotic peptides will produce changes in the amino acid sequence leading to a variant form of two-component lantibiotic having one or more different properties compared to naturally occurring lantibiotic. Similarly, mutations of the modifying enzymes can lead to different post-translational modifications. Such mutagenesis can be performed using available methods, e.g., chemical mutagenesis, alanine-scanning mutagenesis, site-directed mutagenesis using oligonucleotides, error-prone PCR or by propagating target nucleic acid in an appropriate plasmid in a mutator strain, e.g., the XL1-Red strain of *E. coli* (STRATAGENE). The protocol for this procedure is described in Greener and Callahan (1993) STRATEGIES 6:32-34. Mutagenesis can be carried out on a particular coding sequence (e.g., HalA1, HalA2, HalM1, or HalM2) or the entire gene cluster encoding the biosynthetic machinery for lantibiotic production can be subjected to mutagenesis.

In some embodiments, the present invention provides a method for producing a library of lantibiotic-producing host cells, wherein the host cells produce mutant forms of haloduracin. Such a library can be screened for desirable properties. Desirably, the library is initially screened for lantibiotic production (e.g. by determining the effect on *Lactococcus lactis* growth), and then screened for interesting and/or advantageous mutations. Subsequent screening can be limited, e.g., following such an initial screening step, to host cells which display lantibiotic production. Lantibiotics identified by such a screening method can be purified and used in accordance with the pharmaceutical compositions and therapeutic methods disclosed herein.

Having demonstrated the isolation and production of a biologically active two-component lantibiotic from *Bacillus*, the present invention also relates to two-component *Bacillus* lantibiotic compositions and methods for use in pharmaceutical, agricultural, and food industry applications to combat infections caused by strains of *Actinobacilli*, *Clostridium* sp., *Corynebacteria*, *Enterococci*, *Listeria monocytogenes*, *Mycobacterium phlei*, *Neisseria*, *Propionibacterium*, *Staphylococci*, *Streptococci*, and other Gram-positive bacteria. In this regard, the present invention relates to methods for preventing or inhibiting the growth of a bacterium and preventing or treating a bacterial infecting by providing an effective amount of a two-component *Bacillus* lantibiotic disclosed herein. Such an effective amount provides a measurable reduction or inhibition in the growth or proliferation of the bacterium.

Thus according to particular embodiments of the present invention, the instant two-component *Bacillus* lantibiotic is provided in pharmaceutical compositions containing, as active ingredient, the lantibiotic in admixture with one or more pharmaceutical carriers and/or excipients. The term pharmaceutical composition as used herein is meant to cover human treatment and prophylaxis as well as the veterinary field. Treatment of animals such as cow (mastitis), chicken and the like are within the scope of the present invention.

For pharmaceutical administration, the two-component *Bacillus* lantibiotic can be incorporated into preparations in either liquid or solid forms using carriers and excipients conventionally employed in the pharmaceutical art, optionally in combination with further active ingredients. The preparation can, for example, be applied orally, parenterally enterally or preferably topically. Preferred forms include, for example, solutions, emulsions, gels, sprays, lotions, ointments, creams or powders. A generally recognized compendium of such preparations is Remington: The Science and Practice of Pharmacy, Alfonso R. Gennaro, editor, 20th ed. Lippincott Williams & Wilkins: Philadelphia, Pa., 2000. The carrier(s) or excipient(s) selected must be acceptable in the sense of being compatible with the other ingredients of the formulation and not injurious to the subjected receiving treatment.

It is contemplated that one of ordinary skill can readily determine the amount of two-component *Bacillus* lantibiotic to be administered. It is apparent that the dosage will be dependent on the particular treatment used. It should also be clear that the dosage should be chosen to display the biological activity without causing adverse effects. It will be understood that age, sex, type of disease, of formulation and other variables known to the person of ordinary skill will affect determination of the dosage to be used.

Advantageously the pharmaceutical compositions can be formulated as dosage units, each unit being adapted to supply a fixed dose of active ingredient. The total daily dose can, of course, be varied depending on the subject treated and the particular use of the composition. Such adjustment can be readily made by the skilled clinician or veterinarian.

If under certain conditions, it would be beneficial to provide a subject with a longer circulating time and/or slow release of the two-component *Bacillus* lantibiotic, the lantibiotic can be trapped in well-known delivery molecules such as liposomes, synthetic vesicles, nanoerythrosomes (U.S. Pat. No. 5,653,999) and the like, according to known methods.

In foodstuff compositions, wherein the instant two-component *Bacillus* lantibiotic prevents solid or liquid food from spoiling (i.e. meats, dowry products, beer, wine and the like) by inhibiting or killing bacteria and especially harmful bacteria, it is contemplated that the instant lantibiotic can be added directly to the food. Furthermore, the instant lantibiotic can be used as biopreservative agent in foods and in personal hygiene products as well as a anticarries agent (i.e., in toothpaste, mouth wash, and in topical application), disinfectant cleanser (to combat acne for example), selective agent against Gram-positive bacteria in culture media (Ray (1992) In: *Food Biopreservative of Microbial Origin*, Ray et al. (Eds) CRC Press Inc., Boca Raton, Fla., p. 207-264; Harlanda (1993) In: *Bacteriocins of Lactic Acid Bacteria*, Hoover et al (Eds.) Acad. Press Inc., San Diego, Calif., p. 63-91; U.S. Pat. No. 5,231,013).

In some embodiments, the instant lantibiotic is provided as a prodrug. The term "prodrug" refers to compounds that are rapidly transformed in vivo to yield the parent compound, for example, by hydrolysis in blood. A thorough discussion is provided in Higuchi and Stella, *Prodrugs as Novel Delivery Systems*, Vol. 14 of the A.C.S. Symposium Series, and in *Bioreversible Carriers in Drug Design* (1987) Edward B. Roche (ed.) American Pharmaceutical Association and Pergamon Press.

Such a prodrug includes esters or amides of the instant alpha and beta peptides. Examples of pharmaceutically acceptable, non-toxic esters of said peptides include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. As will be appreciated by the skilled artisan, such esters can be prepared according to conventional methods.

Examples of pharmaceutically acceptable, non-toxic amides of the lantibiotic peptides of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom. As with the esters, amides of the instant alpha and beta peptides can be prepared according to conventional methods.

The invention is described in greater detail by the following non-limiting examples.

Example 1

Materials

*Bacillus halodurans* C-125 was purchased from the American Type Culture Collection (ATCC, Manassas, Va.). The bioactivity indicator strain *Lactococcus lactis* CNRZ 117 was obtained from the Centre National de Recherches Zootechniques (Jouy-enJosas, France). Genomic DNA isolated from *B. halodurans* C-125 was also purchased from the ATCC. Chemically competent *Escherichia coli* DH5α cells were purchased from the UIUC Cell Media Facility, while electrocompetent BL21 (DE3) cells were purchased from STRATAGENE (La Jolla, Calif.). Media was obtained from DIFCO Laboratories (Sparks, Md.). Oligonucleotide primers were synthesized by Operon Technologies (Alameda, Calif.). Cloned Pfx polymerase, T4 DNA ligase, and restriction enzymes NdeI, NheI, BamHI, and XhoI were obtained from INVITROGEN (Carlsbad, Calif.). Factor Xa was obtained from NEW ENGLAND BIOLABS (Ipswich, Mass.). Cloning vectors (pET) were purchased from NOVAGEN (Madison, Wis.). Iodoacetamide was obtained from Acros Organics (Geel, Belgium). DTT (1,4 dithio-DL-threitol) was purchased from FISHER BIOTECH (Hampton, N.H.) and TCEP (tris(2-carboxyethyl) phosphine hydrochloride) was obtained from Sigma-Aldrich (St. Louis, Mo.). IPTG (isopropyl-1-thio-Dgalactopyranoside) was obtained from CALBIOCHEM (San Diego, Calif.). C-18 zip tips were purchased from MILLIPORE (Billerica, Mass.). Gel extraction, plasmid mini-prep, and PCR purification kits were purchased from QIAGEN (Valencia, Calif.). A 5 mL HITRAP chelating HP column and PD-10 columns were purchased from GE Healthcare. Thiopropyl SEPHAROSE resin was purchased from Amersham Biosciences (Piscataway, N.J.). Dialysis tubing (SPECTRA/POR) was obtained from Spectrum Laboratories, Inc. (Rancho Dominguez, Calif.). The ketone modifying agents 1,2-phenylenediamine and benzoyl hydrazine were purchased from Sigma-Aldrich and Alfa Products, Thiokol/Ventron Division (Danvers, Mass.), respectively.

Example 2

Methods

Induction of Haloduracin Production. *B. halodurans* C-125 was obtained as a freeze-dried culture and rehydrated using trypticase soy broth (pH 7 and 9) under aerobic conditions at 37° C. A 5 mL culture of *B. halodurans* C-125 was inoculated from this cell stock in LB broth and grown under aerobic conditions for 30 hours at 37° C. Aliquots of the culture (100 μL) were removed and plated on modified nutrient agar. The plates were grown an additional 90 hours at 30° C. until a dense lawn of bacteria was present. Bacterial lawns were gently washed with sterile water to remove the cells from the plate. The cell suspension was collected and incubated overnight at 30° C. without shaking to further induce sporulation. The solution was then centrifuged at 5000×g for 30 minutes at 4° C. and the supernatant was filtered using a 0.2 μm syringe filter to remove any remaining cells or spores. The cell-free solution containing haloduracin was analyzed by mass spectrometry and used for bioassays.

Mass Spectrometry. Matrix-assisted laser desorption ionization-time of flight (MALDI-TOF) mass spectrometry was performed using a Voyager-DE-STR (APPLIED BIOSYSTEMS, Foster City, Calif.) instrument. Assay samples were prepared for MS by purification over a C-18 zip tip. The sample was eluted from the zip tip into a saturated solution of α-hydroxycinnamic acid prepared in 50% acetonitrile containing 0.1% trifluoroacetic acid (TFA) for analysis. High resolution ESI-FTMS was performed on a custom-built 8.5 T Quadrupole—FTMS (Miller, et al. (2006) *J. Am. Chem. Soc.* 128:1420-1; Patrie, et al. (2004) *J. Am. Soc. Mass Spectrom.* 15:1099-108). The fragment ion prediction program of the ProSight PTM software bundle was used to generate fragment ion masses.

Bioactivity Assay. The inhibitory activity of haloduracin isolated from the producing strain and prepared in vitro was assayed using the solid agar medium test. Liquid molten GM17 agar (4% M17, 0.5% glucose, 1.5% agar) was cooled to 50° C. and seeded with an overnight culture of the indicator strain *Lactococcus lactis* CNRZ 117. After agar solidification in a Petri dish, samples were applied to a small well created in the medium. Assay samples were typically concentrated to dryness using a speed vac and rehydrated in a small volume (5-15 μL) of sterile water for application purposes. The cell-free solution isolated from *B. halodurans* C-125 was applied directly to the plate without further concentration. Plates were incubated overnight at room temperature and zones of inhibition were observed the next day.

Molecular Cloning of Haloduracin Expression Constructs. Genomic DNA from *B. halodurans* C-125 was used as the template for PCR amplification of halA1, halA2, halM1, and halM2. Primers (Table 1) were constructed that added an NdeI restriction site 5' and XhoI restriction site 3' to each halA gene. An NheI restriction site was added at the 5' end of halM1, while an XhoI site was added to the 3' end. The halM2 gene was amplified with an XhoI restriction site at the 5' end and a BamHI restriction site at the 3' end. The PCR products were digested with the appropriate restriction enzymes and gel purified using a QIAGEN gel extraction kit. Vector DNA (pET15b for halA1, halA2, halM2 and pET28b for HalM1) digested with the same restriction enzymes was added to a ligation reaction containing T4 DNA ligase and the insert DNA. Chemically competent *E. coli* DH5α cells were transformed with each ligation mixture and plated on LB-agar containing the appropriate antibiotics to screen for positive clones (pET15b based constructs—ampicillin, 100 μg/mL; pET28b based constructs—kanamycin, 50 μg/mL). Clones were screened by redigestion of isolated plasmid DNA or colony PCR. Positive clones were confirmed by DNA sequence analysis.

TABLE 1

| Construct | Location | Primer Sequence | SEQ ID NO: |
|---|---|---|---|
| pHalA1 | 5' | GCGCCGCATATGACAAATCTT | 24 |
|  | 3' | AGGCTCGAGTTAGTTGCAAGA | 25 |
| pHalA2 | 5' | GCGCCGCATATGGTAAATTCA | 26 |
|  | 3' | AAACTCGAGTTAGCACTGGCT | 27 |
| pHalM1 | 5' | GCCGCTAGCATGAGAGAATTA | 28 |
|  | 3' | CGTCTCGAGTTAATGATTCGC | 29 |
| pHalM2 | 5' | GGGTATCCGCTCGAGATGAAAACTCC TCTAACAAGT | 30 |
|  | 3' | TATAAACGCGGATCCTTATCTGTCAT GAATTCTCAA | 31 |
| pHalA1-Xa | 5' | ATTCTAGCTGGGATTGAAGGTCGTTG CGCATGGTAC | 32 |
|  | 3' | AGGCTCGAGTTAGTTGCAAGA | 33 |
| pHalA2-Xa | 5' | GCTTCAGGAGATATTGAAGGTCGTAC AACTTGGCCT | 34 |
|  | 3' | AAACTCGAGTTAGCACTGGCT | 35 |

Engineering of a Factor Xa Cleavage Site in the HalA Peptides. To generate HalA peptides that contained a Factor Xa cleavage site, primers were designed for each peptide that contained the nucleotide sequence necessary to encode the amino acids Ile-Glu-Gly-Arg (SEQ ID NO:9) in place of four wild-type peptide residues. In the first round of PCR to generate a megaprimer for subsequent rounds, the mutations were encoded by the 5' primer, while the 3' primer remained the same as listed in Table 1. The template DNA used for this reaction was the pET15b construct containing the wild-type halA gene cloned previously. The double stranded PCR product of the first round was gel-purified and used as one of the primers in the next round of PCR. The other primer for round two was specific for the T7 promoter of the pET vector in which the gene was originally cloned. Using the megaprimer isolated above and the T7 promoter primer with the DNA of the pET construct containing the wild-type gene as template, a PCR product was generated that contained the appropriate mutations. In the case of HalA1, residues Val-Asn-Gly-Ala (SEQ ID NO:36) were replaced with Ile-Glu-Gly-Arg (SEQ ID NO:9) resulting in the sequence set forth in SEQ ID NO:10, while residues Val-His-Ala-Gln (SEQ ID NO:37) were substituted with Ile-Glu-Gly-Arg (SEQ ID NO:9) in HalA2 resulting in the sequence set forth in SEQ ID NO:11. The DNA was gel-purified and the modified gene of interest was excised from the PCR product by digestion with NdeI and XhoI. Following gel purification, each modified halA gene was ligated into pET15b digested with the appropriate restriction enzymes and transformed into *E. coli* DH5α cells. Positive clones were isolated and confirmed by DNA sequence analysis.

Overexpression and Purification of HalA Peptides. The electrocompetent *E. coli* BL21 (DE3) strain was transformed with the pET construct containing the appropriate N-terminal hexa-histidine halA fusion gene. Cultures were inoculated from single colony transformants and grown overnight at 37° C. in LB broth supplemented with 100 μg/mL ampicillin. The overnight culture was used to inoculate 3 liters of LB broth, and cells were grown at 37° C. to A600 ~0.6-0.8. Expression was induced by the addition of 1 mM IPTG, and the culture was incubated at 37° C. for three additional hours. Cells were harvested by centrifugation at 6500×g for 20 minutes at 4° C. The pellet (~15 grams) was resuspended in 30 mL of start buffer containing 20 mM sodium phosphate, pH 7.5, 20% glycerol, 500 mM NaCl, and 0.5 mM imidazole. The cell paste was subjected to sonication to lyse the cells. Cell debris was removed by centrifugation at 16,500×g for 20 minutes at 4° C. The supernatant was decanted and the pellet containing the insoluble peptide was resuspended in the same volume of start buffer. The sonication and centrifugation steps were repeated and the pellet was resuspended in 30 mL of buffer 1, containing 6 M guanidine hydrochloride, 20 mM sodium phosphate, pH 7.5, 500 mM NaCl, and 0.5 mM imidazole. The sample was sonicated and remaining insoluble material was removed by centrifugation at 16,500×g for 20 minutes at 4° C. and the supernatant passed through a 0.45 μm filter. The peptides were purified by immobilized metal affinity chromatography (IMAC) using a 5 mL $Ni^{2+}$ column. The filtered sample was applied to the column and washed with two column volumes of buffer 1, followed by two column volumes of buffer 2 containing 4 M guanidine hydrochloride, 20 mM sodium phosphate, pH 7.5, 300 mM NaCl, and 30 mM imidazole. The peptide of interest was eluted in 1-2 column volumes of elution buffer containing 4 M guanidine hydrochloride, 20 mM sodium phosphate, pH 7.5, 100 mM NaCl, and 1 M imidazole. The fractions containing peptide were pooled and desalted via dialysis or reverse-phase high-performance liquid chromatography. Dialysis was performed using 1000 Da molecular weight cut off tubing in which the peptide sample buffer was exchanged with 20 mM sodium acetate, pH 4, followed by exchange with 0.05% HCl. Reverse-phase HPLC was performed on a C4 column using a gradient of 2-100% of 80% acetonitrile in 0.1% TFA. Following desalting by either method, the peptide sample was lyophilized to dryness and stored at −20° C.

Overexpression and Purification of the HalM Enzymes. Electrocompetent *E. coli* BL21 (DE3) strain was transformed with the pET construct containing the appropriate N-terminal hexa-histidine halM fusion gene. Cultures were inoculated from single colony transformants and grown overnight at 37° C. in LB broth supplemented with 100 µg/mL ampicillin or 50 µg/mL kanamycin. The overnight culture was used to inoculate 3 liters of LB broth, and cells were grown at 37° C. to A600 ~0.5-0.6. Expression was induced by the addition of 1 mM IPTG, and the culture was incubated at 18° C. for ~20 additional hours. Cells were harvested by centrifugation at 6500×g for 20 minutes at 4° C. The pellet was resuspended in 20 mM Tris, pH 7.6, 500 mM NaCl, and 10% glycerol and lysed by sonication at 65% intensity for 15 minutes. The sample was clarified by centrifugation at 16,500×g for 20 minutes at 4° C. to yield the crude cell-free extract, which was filtered through a 0.45 µm filter.

Each HalM protein was purified by IMAC using a 5 mL $Ni^{2+}$ column. After the sample was applied to the column, it was washed with two column volumes each of 25 mM, 50 mM, and 75 mM imidazole in 20 mM Tris, pH 7.6, 500 mM NaCl, and 10% glycerol. The protein was eluted with two column volumes each of 200 mM and 500 mM imidazole in 20 mM Tris, pH 7.6, 500 mM NaCl, and 10% glycerol. Fractions were analyzed by SDS-PAGE and those containing protein were pooled and desalted using a PD-10 size exclusion column. The protein was stored in 20 mM Tris, pH 7.6, 100 mM or 500 mM KCl, and 10% glycerol at −80° C.

HalM Assays of HalA Substrates. Purified HalA peptides were incubated with purified HalM proteins in various combinations of substrates and enzymes in the presence of 50 mM MOPS, pH 7.2-7.5, 2.5 mM ATP, 1-3 mM TCEP, and 10 mM $MgCl_2$ at 25° C. for 2-4 hours. The final concentration of each peptide or protein was ~0.4 mg/mL. Aliquots were removed at set times and subjected to purification over a C-18 zip tip followed by MALDI-TOF MS analysis.

Iodoacetoamide Modification of Haloduracin. The haloduracin peptides isolated from *B. halodurans* C-125 or produced in vitro were subjected to modification by iodoacetoamide (IAA). Hal1 and Hal2 isolated from *B. halodurans* were incubated with 5 or 10 mM IAA for 30-45 minutes at room temperature in the dark both before and after treatment with 1 mM TCEP to reduce any potential disulfide linkages. HalA1 and HalA2 were analyzed immediately following modification by the HalM enzymes, since excess reductant (TCEP) is present in the assay mixture and keeps all unreacted Cys reduced. Samples were taken for MALDI-TOF MS and excess IAA was removed by addition of ~0.5 mg of thiolpropyl-SEPHAROSE resin in a water-slurry mixture and subsequent centrifugation.

Analysis for an N-terminal 2-Oxobutyryl Group by Diamine Modification. 1,2-Phenylenediamine was added to a 4 M sodium acetate buffer, pH 4.8 to a final concentration of 40 mM. Each peptide was added to this solution at a final concentration of 0.1-0.3 mg/mL for the Hal peptides or 0.03-0.1 mg/mL for the 2-oxobutyryl-Ala-Trp-Pro-Ser (SEQ ID NO:40) synthetic control peptide. Reactions were incubated at 38° C. for 12 hours and analyzed by MALDI-TOF MS. No change in mass was observed for either haloduracin peptide, while the AWPS peptide exhibited a decrease in mass of 84 Da (i.e., 566 Da to 482 Da).

Analysis for an N-terminal 2-Oxobutyryl Group by Hydrazine Modification. The Hal peptides isolated from *B. halodurans* C-125 or the positive control peptide Ala-Trp-Pro-Ser (SEQ ID NO:40) containing a 2-oxobutyryl moiety were incubated in 100 mM MOPS, pH 3 or 5 with 5 mM benzoyl hydrazine at a final concentration of 0.3 mg/mL for 12 hours at 25° C. Samples were analyzed by MALDTOF MS. No change in mass was observed for Hal1 or Hal2, indicating that hydrazone formation did not occur. In contrast, the Ala-Trp-Pro-Ser (SEQ ID NO:40) peptide exhibited a 118 Da increase in mass, consistent with hydrazone formation at the ketone functional group.

Factor Xa Cleavage of Peptide Leader Sequences. Factor Xa was used to remove the leader sequences from the HalA-Xa peptides following modification by the HalM enzymes. Both $CaCl_2$ and Factor Xa were added directly to the HalM assay mixture at final concentrations of 2 mM and 0.03 mg/mL, respectively. Samples were then incubated at room temperature for 3-6 hours to fully proteolyze the peptide substrates. Aliquots were removed for MALDI-TOF MS analysis. Reactions were concentrated to dryness using a speed vac and brought up in ~10-15 µL of sterile water for use in the bioactivity assay.

Example 3

Identification of Haloduracin

During a search for analogs of the lantibiotic mersacidin, a homolog of the mrsA gene was identified in the fully sequenced genome of the Gram-positive bacterium *Bacillus halodurans* C-125 (Takami, et al. (2000) *Nucleic Acids Res.* 28:4317-31). This strain had not previously been reported to produce a lantibiotic. The HalA1 gene encoded a peptide of 69 residues (SEQ ID NO:3), with a 41-residue leader sequence (SEQ ID NO:38) of the double-glycine type that was expected to be removed by a protease resulting in a 28-residue active peptide (SEQ ID NO:5). The HalA1 peptide, found in GENBANK Accession No. BAB04173, shared 34% sequence identity with the precursor peptide for mersacidin. Further analysis of the surrounding DNA sequence identified the halA2 gene immediately 5' of halA1. HalA2, found in GENBANK Accession No. BAB04172, contained 65 residues (SEQ ID NO:4), 35 of which likely encompassed the leader sequence (SEQ ID NO:39) based on a predicted double-glycine cleavage signal at residues Gly34-Ser35 resulting in a 24 amino acid residue active peptide (SEQ ID NO:6). The two prepeptides HalA1 and HalA2 shared 22.9% sequence identity with each other (FIG. 1A). HalA1 has significant sequence identity (40-50%) with peptides from other two-component systems, including LtnA1 (lacticin 3147; Ryan, et al. (1999) *J. Biol. Chem.* 274:37544-50), PlwAα (plantaricin W; Holo, et al. (2001) *Microbiology* 147:643-651), and SacAα (staphylococcin C55; Navaratna, et al. (1998) *Appl. Environ. Microbiol.* 64:4803-8) (FIG. 1B). HalA2 exhibits similarity (35-40% identity) to PlwAα (plantaricin W), CylL-L and CylL-S (cytolysin), and Ltn2 (FIG. 1C).

Inspection of the sequence alignments in FIG. 1B and FIG. 1C as well as the structures of lacticin 3147 and haloduracin reveals similarities and differences in the two component lantibiotics, which with the exception of lacticin 3147 (Weidemann, et al. (2006) *Mol. Micro.* 61:285-296), have not been structurally characterized. The A1/α-peptides all have the same topology of the three C-terminal rings, which is important in lipid II binding in mersacidin. On the other hand, the N-terminus is quite different amongst these peptides, with plantaricin and haloduracin both containing an N-terminal cyclic disulfide, lacticin 3147 and staphylococcin C55 an N-terminal methyllanthionine ring, and the very close homologs BHT and Smb lacking a ring altogether. The A2/β- peptides have structural motifs at both the N- and C-termini. The N-terminal methyllanthionine ring identified herein in HalA2 appears relatively common as sequence homology indicates it is present in all family members accept lacticin 3147 and staphylococcin C55 (FIG. 1C). This first ring is followed by a stretch of hydrophobic amino acids. It is in this region that the Ser to D-Ala conversions occur in LtnA2 of lacticin 3147. The next ring system (B-ring, FIG. 1C) is once again relatively conserved amongst currently known two-component lantibiotics, and is only absent in BHT/Smb. Finally, the two most C-terminal Lan/MeLan rings are conserved in all members that have a companion A1/α peptide. These rings are absent in the two peptides of cytolysin, with CylL$_S$ truncated after the B-ring and CylL$_L$ containing an appended sequence that is unrelated to the other family members.

Two lanM genes, designated HalM1 and halM2, were found flanking the two halA genes and appeared to encode the enzymes that perform the post-translational modification of HalA1 and HalA2. HalM1 (GENBANK Accession No. BAB04174) and HalM2 (GENBANK Accession No. BAB04171) exhibited 25% sequence identity to each other and other LanM proteins from both two-component and single component lantibiotic systems. The leader sequence of the modified HalA peptides was most likely removed by a bifunctional transport protein designated HalT that was also encoded in the gene cluster. HalT contains an N-terminal proteolytic region, six transmembrane regions, and an ATP binding domain and shares homology with the ATP-binding cassette (ABC) family of proteins (Håvarstein, et al. (1995) *Mol. Microbiol.* 16:229-40). The fully modified biosynthetic products, designated Hal1 (from HalA1) and Hal2 (from HalA2), compose the lantibiotic haloduracin and were expected to act synergistically for bactericidal activity.

Including haloduracin, seven two-component lantibiotics have now been documented (Ryan, et al. (1999) *J. Biol. Chem.* 274:37544-50; Holo, et al. (2001) *Microbiology* 147: 643-651; Navaratna, et al. (1998) *Appl. Environ. Microbiol.* 64:4803-8; Yonezawa & Kuramitsu (2005) *Antimicrob. Agents Chemother.* 49:541-8; Hyink, et al. (2005) *FEMS Microbiol. Lett.* 252:235-41). By searching the non-redundant database for homologs to the haloduracin peptides, another gene cluster in *Bacillus licheniformis* was identified that encoded two prepeptides designated herein as LanA1 and LanA2 (FIGS. 2A and 2B, respectively), two modification enzymes designated herein as LanM1 and LanM2, and several additional transport, immunity, and regulation proteins involved in lantibiotic biosynthesis. The amino acid sequence of the lantibiotic prepeptides of *B. licheniformis* as compared to that of haloduracin are depicted in FIGS. 2A and 2B. *Bacillus licheniformis* alpha prepeptide is found as GenBank Accession No. AE017333. The nucleotide sequences encoding LanA1, LanA2, LanM1, and LanM2 are set forth herein as SEQ ID NO:14, SEQ ID NO:15, SEQ ID NO:18, and SEQ ID NO:19, respectively.

Example 4

Production of Haloduracin by *B. halodurans* C-125

Haloduracin production was observed when *B. halodurans* C-125 was grown on modified nutrient broth plates for >90 hours to induce sporulation, which often induces antibiotic production. The plates were washed with sterile water and incubated overnight. Cells and spores were then removed by centrifugation and the supernatant containing the haloduracin peptides was collected. Analysis of the cell-free supernatant by MALDI-TOF mass spectrometry (MS) indicated that two products with masses of 2332 Da (M+H) and 3046 Da (M+H) were present. When applied to a *Lactococcus lactis* CNRZ 117 indicator strain, a zone of growth inhibition was produced. This result demonstrated the isolation of active haloduracin from the producer strain under these conditions.

Example 5

Expression and Purification of the Biosynthetic Components for Haloduracin Production Genomic DNA isolated from *B. halodurans* C-125 was used as the template DNA for PCR amplification of halA1, halA2, HalM1, and halM2. Each gene was cloned into the appropriate pET (NOVAGEN) vector to generate an N-terminal hexa-histidine (H6) fusion construct. The halA genes were overexpressed in *E. coli* and the corresponding peptides purified to homogeneity according to methods used for other lantibiotic prepeptides (Xie, et al. (2004) *Science* 303:679-81). Briefly, the peptides were expressed in inclusion bodies that were isolated by centrifugation and resolubilized in guanidinium hydrochloride. Each peptide was subsequently purified by immobilized metal affinity chromatography (IMAC) followed by reverse-phase high-performance liquid chromatography. Similarly, the halM genes were overexpressed in *E. coli* and the corresponding proteins purified to homogeneity by IMAC, resulting in proteins that were >90% pure.

Purified HalA1 and HalA2 were incubated together with purified HalM1 and HalM2 in an assay mixture containing TCEP (tris(2-carboxyethyl)phosphine hydrochloride), MgCl$_2$, and ATP (Xie, et al. (2004) supra; Chatterjee, et al. (2005) *J. Am. Chem. Soc.* 127:15332-3) and then subjected to MALDI-MS. Incubation of the prepeptides with both modification enzymes resulted in the 3-fold dehydration of HalA1 and the 7-fold dehydration of HalA2 by comparison to the peptide starting material. Based on the number of Ser/Thr residues in the proposed structural regions of HalA1 and HalA2 (FIG. 1), HalA1 underwent three of four possible dehydrations whereas HalA2 was dehydrated at seven of eight possible residues. These results were consistent with the haloduracin peptides isolated from the producer strain whose masses corresponded to the same number of dehydration events for each peptide.

The specificity of each enzyme was subsequently examined. Incubation of HalA1 with HalM1 generated a species that was dehydrated 3-fold, while incubation of HalA2 with HalM2 generated a species that was dehydrated 7-fold. Incubation of HalA1 with HalM2 or HalA2 with HalM1 did not result in modified peptide in either case, indicating that each HalM enzyme can dehydrate one but not both HalA peptides. These data also rule out the possibility that a complex involving both peptides and/or both proteins was required for activity of either enzyme. The activity of HalM1 with HalA1 was examined in the presence of HalA2 as well, and it was found that addition of the non-substrate peptide did not appear to inhibit modification of the true peptide substrate. Similar results were observed for HalM2 with HalA2 in the presence of HalA1.

Example 6

Iodoacetamide Modification of the Haloduracin Peptides

The mass spectra recorded of the HalM assays demonstrated efficient dehydration activity but could not detect cyclization activity since no change in mass occurs in this step. To test for cyclization activity, the substrates and products were monitored for the presence of free cysteines by alkylation with iodoacetamide (IAA) following treatment with a reducing agent to assure cysteines would be available for reaction. Reaction with iodoacetamide results in the addition of a carbamidomethyl group to each free cysteine present, translating to an increase in mass of 58 Da. The authentic Hal1 and Hal2 peptides isolated from *B. halodurans* C-125 were first subjected to IAA modification. Hal1 displayed two adducts as judged by mass spectrometry ($\Delta m=116$ Da). Adduct formation was dependent on prior treatment with a reductant, indicating that the adducts formed on Cys residues that were tied up in a cystine linkage under non-reducing conditions. Hal2 did not undergo IAA adduct formation under any conditions tested, consistent with each Cys residue of this peptide being involved in a MeLan or Lan ring, which were not susceptible to chemical reducing agents.

To determine the importance of the disulfide in Hla1, the bioactivity of Hal1 and Hal2 after chemical modification with iodoacetamide was evaluated after removal of excess iodoacetamide using thiopropyl-SEPHAROSE resin. The remaining peptides containing two (Hal1) or zero (Hal2) adducts were then spotted against the indicator strain, where they exhibited zones of growth inhibition comparable to the wild-type peptides, indicating that the cystine linkage was not necessary for the biological activity of haloduracin.

To compare the ring structures of the haloduracin products produced in vitro with the peptides isolated from the producing strain, the products of the HalM assays were also treated with iodoacetamide and subjected to MALDI-TOF MS. The mass of HalA1 after modification by HalM1 was increased by 116 Da, consistent with the addition of two adducts. The mass of HalA2 modified by HalM2 remained unchanged under the alkylation conditions tested, consistent with the absence of free Cys residues. These results are in agreement with the chemical modification of the wild-type peptides, indicating that the HalM enzymes carried out the in vitro cyclization reaction in the same manner as in vivo.

Example 7

Tests for the Presence of a 2-Oxobutyryl Group

The HalA2 peptide shared sequence homology with the β-peptide of plantaricin W (PlwAβ) and the LtnA2 peptide of lacticin 3147. Both of the mature peptides of these lantibiotics are thought to contain a 2-oxobutyryl group at their N-terminus (Martin, et al. (2004) *Biochemistry* 43:3049-3056; Holo, et al. (2001) *Microbiology* 147:643-651), resulting from spontaneous hydrolysis of an N-terminal Dhb. The position of removal of the leader peptide deduced from the mass of Hal2 isolated from *B. halodurans*, as well as its sequence, indicated Hal2 might also contain a 2-oxobutyryl residue at its N-terminus at position 42 of the prepeptide. To investigate this possibility, the peptide was first reacted with 1,2-diaminobenzene in a sodium acetate buffer to remove the oxobutyryl group (Martin, et al. (2004) supra; Stevens & Dixon (1995) *Biochim. Biophys. Acta* 1252:195-202; Sunde, et al. (1998) *Biochim. Biophys. Acta* 1388:45-52). Analysis by MALDI-TOF, however, did not show any change in the mass of the Hal2 peptide. A control reaction with a synthetic peptide 2-oxobutyryl-Ala-Trp-Pro-Ser (SEQ ID NO:40) showed the expected reaction under identical conditions, indicating that Hal2 did not contain an α-keto amide. In another experiment, rather than removing the 2-oxobutyryl group, the peptide was reacted with benzoyl hydrazine, which should result in a hydrazone adduct if a ketone group were present. However, no adduct was obtained with Hal2, whereas the control peptide showed the expected increase in mass due to hydrazone formation 8 ($\Delta m=118$ Da). Furthermore, the Hal1 and Hal2 peptides were analyzed by high resolution Fourier Transform mass spectrometry (, et al. (2006) *J. Am. Chem. Soc.* 128: 1420-1), which can readily distinguish between peptides of different molecular formula. The masses of HalA1 and HalA2 were 3043.2802 Da (calculated 3043.2730 Da) and 2330.0456 Da (calculated 2330.0469 Da), respectively. The mass of Hal1 was within 2.5 ppm to a product with three dehydrations and one disulfide. The mass of Hal2 was consistent to 0.56 ppm with seven dehydrations and was inconsistent with an N-terminal 2-oxobutyryl group (calculated 2331.0309). Furthermore, analysis of the Hal2 peptide by tandem FTMS/MS resulted in fragment b-ions that clearly showed that in Hal2 Thr1, Thr2, Ser7, and Thr11 were dehydrated (corresponding to Thr42, Thr43, Ser48, and Thr52 in the HalA2 prepeptide) and that the one Ser/Thr residue that was not dehydrated was amongst Thr17, Thr 18, Thr 21 and Ser 22.

Example 8

Engineering a Factor Xa Cleavage Site into the HalA Peptides

The biological activity of lantibiotic peptides is dependent upon the formation of the correct ring structures (Kuipers, et al. (1996) *Antonievan Leeuwenhoek* 69:161-169; Bierbaum, et al. (1994) *Appl. Environ. Microbiol.* 60:4332-8; Chen, et al. (1998) *Appl. Environ. Microbiol.* 64:2335-40; Ottenwälder, et al. (1995) *Appl. Environ. Microbiol.* 61:3894-903) and the removal of the N-terminal leader sequence of the modified peptides (van der Meer, et al. (1994) *J. Biol. Chem.* 269:3555-62; Xie, et al. (2004) *Science* 303:679-81). To demonstrate the biological activity of the haloduracin peptides prepared in vitro, the leader sequence of each product had to be removed. A peptide engineering method was used to achieve this goal. The last four amino acid residues of each peptide N-terminal to the cleavage site (as deduced from authentic Hal1 and Hal2) were replaced with the Factor Xa recognition sequence. In the case of HalA1, residues 38-41 (Val-Asn-Gly-Ala; SEQ ID NO:36) were replaced with the sequence Ile-Glu-Gly-Arg (SEQ ID NO:9) using molecular biology methods, whereas for HalA2 residues 32-25 (Val-His-Ala-Gln; SEQ ID NO:37) were replaced by Ile-Glu-Gly-Arg (SEQ ID NO:9). Because Factor Xa cleaves after the sequence Ile-Glu-Gly-Arg (SEQ ID NO:9), the structural region of each peptide obtained after digestion would correspond to the native mature products. The HalA peptides containing the Factor Xa cleavage site were overexpressed as hexahistidine fusion proteins and purified as described for the wild-type peptides. HalA1-Xa (HalA1 containing the Ile-Glu-Gly-Arg (SEQ ID NO:9) cleavage site) was incubated with HalM1 under the standard assay conditions to generate a 3-fold dehydrated species as judged by MALDI-TOF MS. HalA2-Xa (HalA2 containing the engineered cleavage site) was incubated with HalM2 under the same conditions to generate a 7-fold dehydrated species as judged by MALDI-TOF 9 MS. The results were consistent in both cases with the wild-type peptide data, indicating that substitution of four residues in the leader sequence of each peptide with the sequence Ile-Glu-Gly-Arg (SEQ ID NO:9) did not alter the recognition and activity of the HalM enzymes. Following HalM modification, each peptide was subjected to proteolysis by Factor Xa in a $CaCl_2$-dependent reaction. Application of the proteolyzed samples to the haloduracin sensitive strain *L. lactis* CNRZ 117 resulted in a zone of inhibition comparable to that produced by Hal1 and Hal2 isolated from *B. halodurans*. This zone was dependent on the addition of both modified peptides. When either peptide was spotted separately, no inhibition was observed.

FIG. 3 depicts the structures for the two fully-processed haloduracin peptides that are consistent with mass spectrometric and structural characterization data presented herein, and with structural precedence in peptides from other systems. Based on the high accuracy mass spectrum of Hal1 isolated from the producing strain, HalA1 undergoes 3 dehydration events and the N-terminal leader sequence is removed after the anticipated proteolytic cleavage sequence Gly-Ala. The resulting product retains one Ser residue that was assigned to position 67, on the basis of similarity with the α peptide from plantaricin W (Plwα), which also contains an unmodified Ser residue at the equivalent position (Holo, et al. (2001) supra). The HalA1 structural peptide contains more Cys residues than Ser/Thr and hence not all cysteines can be engaged in Lan/MeLan rings. The formation of two IAA adducts only after pretreatment with reductants indicates that two cysteines are present in a cystine linkage in the isolated peptide. Cys42 and Cys49 are assigned to be involved based on similarity to Plwα. Hal1 is only the third example of a lantibiotic in which Cys residues are present as a disulfide, with sublancin and Plwα being the other examples (Holo, et al. (2001) supra; Paik, et al. (1998) *J. Biol. Chem.* 273:23134-42). As with plantaricin W (Holo, et al. (2001) supra), the oxidation state of these two Cys residues does not seem to be crucial for biological activity, since reduction and even alkylation with IAA did not abolish antimicrobial activity. The three remaining cysteines are believed to form one Lan and two MeLan rings with the same connectivity as confirmed (Martin, et al. (2004) supra) or proposed for all other known two-component lantibiotics (Holo, et al. (2001) supra; Navaratna, et al. (1998) *Appl. Environ. Microbiol.* 64:4803-8; Yonezawa & Kuramitsu (2005) supra; Hyink, et al. (2005) supra). The closest homolog, the α-peptide of plantaricin W, is shown in FIG. 3. The six-amino acid containing MeLan B-ring, which is believed to be important for lipid II binding in mersacidin (Hsu, et al. (2003) *J. Biol. Chem.* 278:13110-7), is conserved in HalA1 and LicA1 including the invariant and essential Glu within this ring (Szekat, et al. (2003) *Appl. Environ. Microbiol.* 69:3777-83). This MeLan ring is also found in the α/A1-peptides of lacticin 3147 (Martin, et al. (2004) supra), plantaricin W (Holo, et al. (2001) supra), staphylococcin C55 (Navaratna, et al. (1998) supra), Smb (Yonezawa & Kuramitsu (2005) supra), and BHT-A (Hyink, et al. (2005) supra) as well as in the lacticin 481 subgroup of single component lantibiotics (Chatterjee, et al. (2005) supra).

The accurate mass for Hal2 isolated from *B. halodurans* C-125 is consistent with 7-fold dehydration of the HalA2 prepeptide and cleavage of the leader peptide C-terminal to Gln41. As for Hal1, the mass data indicate that Hal2 contains one unmodified Ser/Thr residue, assigned to Ser22 based on FTMS/MS data that show the unmodified residue to be located in the segment spanning residues 16-24. Proteolytic processing after Gln41 of HalA2 would result in Dhb42 of HalA2 occupying the N-terminal position of Hal2 upon removal of the leader peptide. Eneamines are unstable in aqueous solutions and undergo spontaneous and rapid hydrolysis to the corresponding ketone, resulting in a 2-oxobutyryl residue instead of a Dhb (Kellner, et al. (1989) *Angew. Chem.* 101:618-21) (see Ltn2 in FIG. 3). Alternatively, if HalM2 catalyzes the formation of an N-terminal MeLan by reaction of Cys46 with Dhb42 of the prepeptide (Dhb1 and Cys5 in mature Hal2), Hal2 would not have an N-terminal Dhb upon proteolysis and hence no α-keto amide would be formed. The IAA alkylation experiments clearly showed that Cys5 of Hal2 was indeed involved in a MeLan since no free Cys was present. Furthermore, three independent methods provided evidence against an N-terminal 2-oxobutyryl group, indicating that HalM2 indeed forms a MeLan between residues 42 and 46 of HalA2. An alternative possibility that would result in the absence of the 2-oxobutyryl group is that Thr42 is not dehydrated resulting in Thr1 at the N-terminus of Hal2 after proteolysis. However, this model is inconsistent with the MS/MS data since the masses of a series of fragment ions clearly indicate the dehydration of Thr1 in Hal2. Unlike Cys5, the remaining three cysteines in Hal2 are conserved in the β/A2 peptides of lacticin 3147, plantaricin W, and staphylococcin C55, and hence their involvement in the Lan and MeLan rings shown in FIG. 3 is supported. Indeed the fragment ions observed are fully consistent with the proposed rings of Hal2, as is the lack of fragmentation in the segments spanning residues 1 and 5, 11 and 15, and 16 to 24 (Xie, et al. (2004) supra).

The mass data demonstrated that the cleavage site for the leader peptide is not at the predicted position as the LanT protease domains typically process their substrates at a double Gly recognition motif; for HalA2 this would have been between Ser35 and Gly36. A similar observation has been reported for the two-component systems plantaricin W and cytolysin, in which the peptide undergoes additional proteolytic processing beyond the removal of the leader sequence (Cox, et al. (2005) supra; Holo, et al. (2001) supra). In cytolysin the additional proteolysis has been shown to be necessary for biological activity (Cox, et al. (2005) supra).

What is claimed is:

1. An isolated two-component lantibiotic of *Bacillus* comprising SEQ ID NO:3 and SEQ ID NO:4; SEQ ID NO:5 and SEQ ID NO:6; SEQ ID NO:7 and SEQ ID NO:8; or SEQ ID NO:10 and SEQ ID NO:11.

2. A pharmaceutical composition comprising the two-component lantibiotic of *Bacillus* of claim 1 in admixture with a pharmaceutically acceptable carrier.

\* \* \* \* \*

SEQUENCE LISTING

```
<160> NUMBER OF SEQ ID NOS: 54

<210> SEQ ID NO 1
<211> LENGTH: 12
<212> TYPE: PRT
<213> ORGANISM: Artificial Sequence
<220> FEATURE:
<223> OTHER INFORMATION: Synthetic alpha peptide sequence
<220> FEATURE:
<221> NAME/KEY: MISC_FEATURE
<222> LOCATION: (3)..(3)
<223> OTHER INFORMATION: Xaa denotes an aliphatic amino acid residue
<220> FEATURE:
<221> NAME/KEY: MISC_FEATURE
<222> LOCATION: (5)..(5)
<223> OTHER INFORMATION: Xaa denotes is any amino acid residue
```

-continued

```
<400> SEQUENCE: 1

Cys Thr Xaa Thr Xaa Glu Cys Met Pro Ser Cys Asn
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic beta peptide sequence
<220> FEATURE:
<221> NAME/KEY: MISC_FEATURE
<222> LOCATION: (10)..(10)
<223> OTHER INFORMATION: Xaa denotes Gln or Arg.

<400> SEQUENCE: 2

Leu Cys Pro Thr Thr Lys Cys Thr Ser Xaa Cys
1               5                   10

<210> SEQ ID NO 3
<211> LENGTH: 69
<212> TYPE: PRT
<213> ORGANISM: Bacillus halodurans

<400> SEQUENCE: 3

Met Thr Asn Leu Leu Lys Glu Trp Lys Met Pro Leu Glu Arg Thr His
1               5                   10                  15

Asn Asn Ser Asn Pro Ala Gly Asp Ile Phe Gln Glu Leu Glu Asp Gln
            20                  25                  30

Asp Ile Leu Ala Gly Val Asn Gly Ala Cys Ala Trp Tyr Asn Ile Ser
        35                  40                  45

Cys Arg Leu Gly Asn Lys Gly Ala Tyr Cys Thr Leu Thr Val Glu Cys
    50                  55                  60

Met Pro Ser Cys Asn
65

<210> SEQ ID NO 4
<211> LENGTH: 65
<212> TYPE: PRT
<213> ORGANISM: Bacillus halodurans

<400> SEQUENCE: 4

Met Val Asn Ser Lys Asp Leu Arg Asn Pro Glu Phe Arg Lys Ala Gln
1               5                   10                  15

Gly Leu Gln Phe Val Asp Glu Val Asn Glu Lys Glu Leu Ser Ser Leu
            20                  25                  30

Ala Gly Ser Gly Asp Val His Ala Gln Thr Thr Trp Pro Cys Ala Thr
        35                  40                  45

Val Gly Val Ser Val Ala Leu Cys Pro Thr Thr Lys Cys Thr Ser Gln
    50                  55                  60

Cys
65

<210> SEQ ID NO 5
<211> LENGTH: 28
<212> TYPE: PRT
<213> ORGANISM: Bacillus halodurans
<220> FEATURE:
<221> NAME/KEY: MOD_RES
<222> LOCATION: (18)..(18)
<223> OTHER INFORMATION: Abu
```

```
<220> FEATURE:
<221> NAME/KEY: MOD_RES
<222> LOCATION: (20)..(20)
<223> OTHER INFORMATION: Abu

<400> SEQUENCE: 5

Cys Ala Trp Tyr Asn Ile Ala Cys Arg Leu Gly Asn Lys Gly Ala Tyr
1               5                   10                  15

Ala Xaa Leu Xaa Val Glu Ala Met Pro Ser Ala Asn
            20                  25

<210> SEQ ID NO 6
<211> LENGTH: 24
<212> TYPE: PRT
<213> ORGANISM: Bacillus halodurans
<220> FEATURE:
<221> NAME/KEY: MOD_RES
<222> LOCATION: (1)..(1)
<223> OTHER INFORMATION: Abu
<220> FEATURE:
<221> NAME/KEY: MOD_RES
<222> LOCATION: (2)..(2)
<223> OTHER INFORMATION: Dehydrobutyrine
<220> FEATURE:
<221> NAME/KEY: MOD_RES
<222> LOCATION: (7)..(7)
<223> OTHER INFORMATION: Dehydrobutyrine
<220> FEATURE:
<221> NAME/KEY: MOD_RES
<222> LOCATION: (17)..(17)
<223> OTHER INFORMATION: Abu
<220> FEATURE:
<221> NAME/KEY: MOD_RES
<222> LOCATION: (18)..(18)
<223> OTHER INFORMATION: Dhb
<220> FEATURE:
<221> NAME/KEY: MOD_RES
<222> LOCATION: (21)..(21)
<223> OTHER INFORMATION: Abu

<400> SEQUENCE: 6

Xaa Xaa Trp Pro Ala Ala Xaa Val Gly Val Ala Val Ala Leu Ala Pro
1               5                   10                  15

Xaa Xaa Lys Ala Xaa Ser Gln Ala
            20

<210> SEQ ID NO 7
<211> LENGTH: 74
<212> TYPE: PRT
<213> ORGANISM: Bacillus licheniformis

<400> SEQUENCE: 7

Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70

<210> SEQ ID NO 8
<211> LENGTH: 50
<212> TYPE: PRT
<213> ORGANISM: Bacillus licheniformis
```

-continued

```
<400> SEQUENCE: 8

Val Ser Glu Glu Glu Leu Lys Ala Leu Val Gly Gly Asn Asp Val Asn
1               5                   10                  15

Pro Glu Thr Thr Pro Ala Thr Thr Ser Ser Trp Thr Cys Ile Thr Ala
            20                  25                  30

Gly Val Thr Val Ser Ala Ser Leu Cys Pro Thr Thr Lys Cys Thr Ser
        35                  40                  45

Arg Cys
    50

<210> SEQ ID NO 9
<211> LENGTH: 4
<212> TYPE: PRT
<213> ORGANISM: Artificial Sequence
<220> FEATURE:
<223> OTHER INFORMATION: Synthetic protease cleavage sequence

<400> SEQUENCE: 9

Ile Glu Gly Arg
1

<210> SEQ ID NO 10
<211> LENGTH: 69
<212> TYPE: PRT
<213> ORGANISM: Artificial Sequence
<220> FEATURE:
<223> OTHER INFORMATION: Synthetic haloduracin

<400> SEQUENCE: 10

Met Thr Asn Leu Leu Lys Glu Trp Lys Met Pro Leu Glu Arg Thr His
1               5                   10                  15

Asn Asn Ser Asn Pro Ala Gly Asp Ile Phe Gln Glu Leu Glu Asp Gln
            20                  25                  30

Asp Ile Leu Ala Gly Ile Glu Gly Arg Cys Ala Trp Tyr Asn Ile Ser
        35                  40                  45

Cys Arg Leu Gly Asn Lys Gly Ala Tyr Cys Thr Leu Thr Val Glu Cys
    50                  55                  60

Met Pro Ser Cys Asn
65

<210> SEQ ID NO 11
<211> LENGTH: 65
<212> TYPE: PRT
<213> ORGANISM: Artificial Sequence
<220> FEATURE:
<223> OTHER INFORMATION: Synthetic haloduracin

<400> SEQUENCE: 11

Met Val Asn Ser Lys Asp Leu Arg Asn Pro Glu Phe Arg Lys Ala Gln
1               5                   10                  15

Gly Leu Gln Phe Val Asp Glu Val Asn Glu Lys Glu Leu Ser Ser Leu
            20                  25                  30

Ala Gly Ser Gly Asp Ile Glu Gly Arg Thr Thr Trp Pro Cys Ala Thr
        35                  40                  45

Val Gly Val Ser Val Ala Leu Cys Pro Thr Thr Lys Cys Thr Ser Gln
    50                  55                  60

Cys
65
```

```
<210> SEQ ID NO 12
<211> LENGTH: 210
<212> TYPE: DNA
<213> ORGANISM: Bacillus halodurans

<400> SEQUENCE: 12
atgacaaatc ttttaaaaga atggaaaatg cctcttgagc gtactcataa taattctaat      60
ccagcagggg atattttcca agagttagaa gaccaagata ttctagctgg ggtgaatggt     120
gcttgcgcat ggtacaacat cagctgccgt ctaggtaaca aaggtgctta ctgcacactt     180
acagttgagt gcatgccttc ttgcaactaa                                      210

<210> SEQ ID NO 13
<211> LENGTH: 198
<212> TYPE: DNA
<213> ORGANISM: Bacillus halodurans

<400> SEQUENCE: 13
atggtaaatt caaaagattt gcgtaatcct gaattccgca aagcccaagg tctacaattc      60
gttgacgagg tgaacgagaa ggaactttcg tctctagctg gttcaggaga tgtgcatgca     120
caaacaactt ggccttgcgc tacagttggt gtctccgtag ccttgtgccc aactacaaag     180
tgtacaagcc agtgctaa                                                   198

<210> SEQ ID NO 14
<211> LENGTH: 225
<212> TYPE: DNA
<213> ORGANISM: Bacillus licheniformis

<400> SEQUENCE: 14
atgtcaaaaa aggaaatgat tctttcatgg aaaaatccta tgtatcgcac tgaatcttct      60
tatcatccag cagggaacat ccttaaagaa ctccaggaag aggaacagca cagcatcgcc     120
ggaggcacaa tcacgctcag cacttgtgcc atcttgagca agccgttagg aaataacgga     180
tacctgtgta cagtgacaaa agaatgcatg ccaagctgta actaa                     225

<210> SEQ ID NO 15
<211> LENGTH: 199
<212> TYPE: DNA
<213> ORGANISM: Bacillus licheniformis

<400> SEQUENCE: 15
tgaaaacaat gaaaaattca gctgcccgtg aagccttcaa aggagccaat catccggcag      60
ggatggtttc cgaagaggaa ttgaaagctt tggtaggagg aaatgacgtc aatcctgaaa     120
caactcctgc tacaacctct tcttggactt gcatcacagc cggtgtaacg gtttctgctt     180
cattatgccc aacaactaa                                                  199

<210> SEQ ID NO 16
<211> LENGTH: 3180
<212> TYPE: DNA
<213> ORGANISM: Bacillus halodurans

<400> SEQUENCE: 16
atgagagaat tacaaaatgc tctttacttt tcagaagtag tgttcgggcc aaatttggag      60
aaaatagttg gtgagaaacg gttgaatttt tggctgaagt tgatcgggga ggatcctgaa     120
aaccttaagg agtttctctc gcgaaaaggg aattcttttg aagaacaaac gctcccggaa     180
aaagaagcga tcgtaccgaa cagattagga gaagaggcac tagaaaaagt aagagaagaa     240
ttggaatttc ttaatacata ttcaacgaag catgtaagaa gagtaaaaga actcggtgtc     300
```

```
caaattccat tgaaggcat tcttctgccg ttcatatcca tgtatataga gaaatttcaa       360
caacaacaat tgaggaaaaa aattggtcca atacatgaag agatttggac tcagatagtg       420
caagatatta ccagcaaact taatgctatt ctacaccgta cacttatcct ggaactgaac       480
gttgcaagag tcacctctca gttgaaggga gataccccgg aagaacgatt tgcttattac       540
tcaaaaacct atttagggaa aagggaggtc acccatcgtc tttattctga atatccagtt       600
gtcctacgat tactatttac cacgattagt catcatatta gctttataac ggaaattctc       660
gaacgagttg ccaacgatcg agaagcgata gaaacagagt tttcaccatg ctcaccgatc       720
ggtactttgg cctcactcca cctaaattca ggtgacgctc atcataaaca acgcacggtc       780
actattctag agttttcttc gtcgttaaaa cttgtttata aaccgcgttc tcttaaggtt       840
gacggggtat ttaatggcct gcttgcattt ttaaatgaca gaacaggtga agtgataaaa       900
gatcaatatt gtcctaaagt gctacaacga gacggatatg gatacgtaga attcgttacc       960
catcaaagct gtcaatcgct agaagaggta tctgattttt atgaaagact cggttcactt      1020
atgagccttt cgtatgtcct caattcatcc gactttcact ttgaaaatat tattgctcat      1080
ggtccatacc ctgttttaat tgatttagag acgattattc ataatacggc cgattcatca      1140
gaagagacat ccacagcgat ggatagagct tttcggatgt aaatgattc tgtcctttca       1200 acaggtatgc taccttcgtc tatctactat cgagatcaac cgaatatgaa agggttaaac      1260
gtaggtggtg tcagcaagag cgagggacag aaaacaccat ttaaagtcaa tcaaattgca      1320
aacagaaata cggatgaaat gagaatagag aaagaccatg tgacgctttc tagtcaaaag      1380
aacttgccaa ttttcaatc ggcagcaatg gagtctgttc actttctcga ccaaattcaa       1440
aagggcttta cttcaatgta tcaatggatt gaaaaaaaca agcaggaatt taaggaacag      1500
gtgcggaagt ttgaaggtgt ccccgtccgg gcggtcctcc gttccacgac acgttatacg      1560
gaacttttaa aaagtagtta tcatccagat ttactaaggt cagcacttga tcgtgaagtt      1620
ctcttaaaca ggttgacggt agattctgtc atgaccccat atttgaagga aattattcct      1680
ctcgaagtgg aagatttact taatggggat gttccatatt tctatacttt gccggaagaa      1740
cgcgccttat atcaagaggc ttccgctatc aattcaacgt ttttaccac atctattttt       1800 cataaaatcg atcaaaaaat agataaatta gggatagagg atcatactca gcaaatgaaa      1860
attttgcata tgtcgatgct tgcaagtaac gcgaatcatt atgcagatgt tgcagacctt      1920
gatattcaaa aaggtcatac gatcaaaaat gagcagtatg tagagatggc aaaagatatt      1980
ggagattact tgatggaatt atctgtggaa ggagaaaatc agggtgaacc tgatctttgt      2040
tggatcagta cggttttaga aggctctagc gaaattatat gggatatttc cccggtaggt      2100
gaagatctat ataatggttc agcaggggtc gccctatttt atgcttactt gtttaaaata      2160
acaggggaga agcgatatca agagatcgcc tataaagcgt tagtccctgt tcggagatct      2220
gttgctcaat tccaacacca ccctaactgg agcataggtg catttaatgg agcgagtggt      2280
tatctttacg caatgggaac aatcgctgct ttatttaatg acgagcgtct taaacatgag      2340
gtaactagaa gcatccctca tatagagcct atgatccacg aagataaaat ctatgatttc      2400
attgggggtt cagcagggc gttgaaagta tttttatctc tttccggcct ttttgatgag       2460
cctaagttct tggaattggc gattgcttgt agtgaacatt taatgaaaaa tgcgatcaag      2520
actgaccagg ggataggatg gaaaccacca tgggaggtaa ctccattaac gggttttttct      2580 catgcgtat caggcgtaat ggcttcgttc attgaactct atcaacagac tggagatgaa       2640
cggctgttat cctatattga tcaatctctt gcgtatgagc gaagtttctt ttcagaacag      2700
```

-continued

```
gaggaaaact ggctaactcc aaacaaagaa acgccagttg ttgcgtggtg ccatggggcg      2760
ccagggatac ttgtaagtcg cttactatta aagaaatgtg gatatcttga tgagaaggta      2820
gaaaaagaga ttgaagtggc cttgtctaca acgataagaa aaggtcttgg taacaatcgt      2880
tccctttgcc acggtgactt tggccaattg gagattttac gatttgcggc cgaggtttta      2940
ggcgattcgt atttacagga agtagtaaac aatctcagtg gtgagttgta caatcttttc      3000
aaaacagaag ggtatcagtc gggaacctct agaggaacgg aatccgttgg tttaatggtg      3060
gggctgtctg gatttggtta tggactttta agtgctgctt atccatctgc cgttccttct      3120
atactaacgc tagacggcga aattcaaaaa taccgtgaac cgcatgaggc gaatcattaa      3180
```

<210> SEQ ID NO 17
<211> LENGTH: 2973
<212> TYPE: DNA
<213> ORGANISM: Bacillus halodurans

<400> SEQUENCE: 17

```
atgaaaactc ctctaacaag tgagcatcct agcgtaccaa caacacttcc gcacaccaac        60
gatacagatt ggctagaaca acttcatgac atcttatcga tccctgtcac cgaagagatc       120
cagaaatact tccatgcaga aaatgatttg ttttcttttt tctatactcc ctttcttcaa       180
tttacatatc aatcaatgtc cgactatttt atgactttca aaacggacat ggcgctcata       240
gaacggcaat cacttctaca atcaaccttaa acagctgttc accatcgcct ctttcactta      300
actcatcgta cgttaatttc agaaatgcac attgataaat taactgtagg cttaaacgga       360
tcaacaccac acgaacgtta tatggatttt aaccataaat ttaataaaac ttcaaaatca       420
aaaaatttat ttaatatata tccaattcta ggtaaacttg tagtaaatga gacgttgcgc       480
accatcaatt ttgtaaaaaa gatcattcag cattatatga aagactacct attgttgagt       540
gattttttta aagagaaaga cttacgacta acgaaccttc agctcggcgt cggggatact       600
catgtaaatg gtcaatgtgt gaccatcctt acatttgcct ctggccaaaa agtagtctac       660
aagccccgtt ccctgtcaat tgataaacaa tttggtgagt ttattgagtg ggttaattcc       720
aaaggatttc aaccatcatt acgcattcct atagccattg atcgacaaac atacggctgg       780
tatgaattta tcccacatca agaggcaaca tcggaggatg agatcgagcg ctattattca       840
agaatcggag gatatctggc tatcgcttat cttttcggag cgacagatct tcatttagac       900
aatttaatcg cctgcggaga acacccgatg ttaattgatt tagaaacatt attcaccaat       960
gatttggatt gttacgacag cgcatttcca ttccctgctc ttgctaggga gctaacacaa      1020
tctgtctttg ggaccttgat gcttccaatt acaattgcta gtggcaaatt acttgatatc      1080
gatctaagtg cagtcggcgg gggaaaaggc gttcaatctg aaaagattaa acatgggtt      1140 atcgtcaatc aaaaaacgga tgagatgaag ttagttgaac aaccttacgt aaccgaatct      1200
agccaaaata aacctacagt taacgggaaa gaagcgaata tcgggaatta catccccat       1260 gttacagatg gttttcggaa aatgtatcga ctctttctca acgaaatcga tgaactaatg      1320
gaccacaacg ggcctatctt cgcttttgaa tcatgtcaaa ttcgccatgt gtttcgggcc      1380
actcatgttt atgctaaatt tttggaggct agcactcacc ccgactattt gcaggaaccg      1440
actaggcgga ataagctgtt tgaatcattc tggaacatta cctcgttaat ggctccattt      1500
aagaagatcg tgccacatga aatagcagaa cttgaaaacc atgatatccc ttattttgtc      1560
cttacttgtg gcggaaccat cgttaaggat ggatatggaa gagacatcgc tgacctcttt      1620
caatcctctt gtattgaacg agtcacccat cgactacaac agttagggag tgaagatgaa      1680
```

```
gcaagacaaa ttcgctatat caagagctct cttgctaccc ttactaatgg cgactggaca    1740
ccttctcacg aaaaaacacc aatgtcacct gcttctgctg accgagaaga tggatacttt    1800
ttgcgagaag cccaagccat aggagatgac attttagcgc aactcatttg gaagacgat     1860
cggcatgccg cttatttaat tggtgtaagt gttggaatga atgaagccgt aaccgtctcc    1920
cctctcacac cagggattta tgatggtaca ttaggaattg ttttgttttt cgatcaactt    1980
gctcaacaaa caggagaaac acactaccgg catgctgctg atgctttgtt ggaaggaatg    2040
tttaaacagc taaagcctga gctaatgcca tcttctgctt atttcggttt agggtcactg    2100
ttctatggcc ttatggtgct ggactccaa cggtctgatt cacacatcat tcaaaaggca    2160
tatgaatact tgaagcattt ggaagaatgt gttcagcacg aagaaacacc ggactttgtc    2220
agtggtttat ctggagttct ttatatgctg acaaaaatct atcaactgac aaacgagcct    2280
agagttttg aggtagcaaa gacgaccgca agccgattgt cagtgctatt agattctaaa     2340
cagccagata cggttcttac ggggcttagc catggagccg caggatttgc gttagcttta    2400
ctcacttacg gaacggctgc gaatgatgaa cagcttttga acaagggca ctcgtacctt     2460
gtctatgaac ggaaccgatt taacaaacag gaaacaatt gggtggattt aaggaaggga    2520
aacgcctatc aaacctttg gtgccatggt gctcctggga ttgggatcag ccgtctttta    2580
ctagcacagt tctacgatga cgaacttctt cacgaagaat taaatgctgc attaaacaaa    2640
accatatcag acgggttcgg gcataatcat agtctctgtc acggtgattt cggaaattta    2700
gatcttttac tgttgtatgc ccagtatacg aacaatcccg agccaaaaga gctagcaaga    2760
aaattagcga tttcttctat cgaccaagcg cacacatatg gctggaaatt gggcttaaat    2820
catagcgatc aattgcaagg aatgatgtta ggggtcacag gtattggcta tcaattgctt    2880
cgacatatta accctaccgt tccatcgatt ttagcactgg agcttccctc ttctacatta    2940
accgaaaaag agttgagaat tcatgacaga taa    2973
```

<210> SEQ ID NO 18
<211> LENGTH: 3159
<212> TYPE: DNA
<213> ORGANISM: Bacillus licheniformis

<400> SEQUENCE: 18

```
atgaatgaaa aatccgccgg atatcacgaa cggcttcccg tcgcccaaac tcaatccccg     60
ctcgtaaacg ataagataaa gtattggcgt tcccttttcg gcgatgatga taaatggctc    120
aataaagcag tttcattatt aagccatgac cctttgtcct ccatcgcaca atcctcggta    180
tcccagtcag tcgggctgaa agacagccgt cgcggcccat ggcagaagat gcaaaagcgg    240
atctttgaaa cgcccttttc ctacaaggat tctgctctgc aagattcaga attgctgttc    300
gactccctgc tgacccgttt tgcgtctgca gcacaagatg ctttggagga acaaaatatc    360
atactttctc ctcctctttg ccggcaggtg ctgacacatt taaaacagac gcttcttcaa    420
attgcccatc aaacattaat actggaacta aacatttta ggcttgaaga tcaattgaag     480
ggcgacaccc ccgaaatgcg ctatcttgat ttcaatgata cttttttagt caatccagga    540
tacctgcgga ccctgttcaa cgagtatccc gtattgctgc gccttctgtg cacaaaaacc    600
gattactggg ttcaaaactt ttctgaactg tggaagaggc tgaggcagga ccgcgaacag    660
ctgcaggctg catttcatat tgccggcgat cctgtccata ttgagcttgg ggtgggagac    720
tcgcacaata aaggaaagat ggcagccatc cttacatatt ccgatggaaa aaagattgtc    780
tataaaccga gaagccatga tgttgacgac gcatttcaac ttcttctatc atggatcaat    840
```

```
gaccgaaatt caggcagccc tttaaaaact ttgagattaa tcaataaaaa acggtacgga    900
tggtccgagt ttattcctca cgaaacgtgc catacgaaaa aagaactgga aggctactat    960
acacgcctcg gcaaactttt ggccgtttta tacagcatcg atgccgttga cttccaccac   1020
gaaaacatta tcgcctccgg cgagcatcct gttttaatcg atcttgaatc aattttcat    1080
caatataaaa aacgagacga acccggctcg accgccgttg acaaagcaaa ctacattctt   1140
tccagatccg tacggtctac cggaatcctg ccgttcaacc tttacttcgg aaggaaaaac   1200
cgggataaag ttgtggacat cagcggaatg ggggggcagg aagctcagga atcaccgttt   1260
caggcgcttc aaatcaaagg attttccgc gatgacattc gcctggagca tgaccgattt    1320
gaaatcggcg aggcgaaaaa tctgccgact ttagatcacc agcatgtccc tgtcgcagat   1380
tatcttcatt gtatcatcga aggattttca gcagtatacc gtctgatttc tgatcatggc   1440
gaaagctacc tggctacgat tgaacatttt aaaaactgca ccgttcgaaa tattttgaag   1500
ccgacagcgc actacgcctc tcttttgaat aaaagctacc accctgattt tctcagggat   1560
gcggtagacc gtgaagtgtt tttatgccgg gtggaaaagt ttgaagatgc agacacagat   1620
attgcagcgg caaaaacaga gctgaaagag ctcattcggg gagacatccc ctattttctg   1680
tcgaagcctt cagataccta tttgctcaat ggcgaagaag aaccgattgc cgcttatttt   1740
gaaacgccgt ccttcacaag agtaattaag aagatctcat cattttcaga ccaggactta   1800
aaggaacaag cgaatgtcat acgcatgtcg attctggctg catataacgc gagacatgaa   1860
aaagacgcaa tcgatataga ccaaaatcac ccgagtccta gatcaggcgc cttgcagccg   1920
ctcgccatcg ctgagaaagc ggctgacgat ttggctgaaa agcgaattga aggcaatgat   1980
ggaaaggacg tcacttggat cagtacagtt attgaaggcg tcgaagaaat ctcttggacg   2040
atctcccctg tcagtcttga tttatataat ggcaatgcag gcatcggact ttttatgagc   2100
tatctgagcc gcttcgcaaa acggccggag acttactcgc atataaccga gcagtgtgta   2160
tttgcgattc agcgagcgtt gaatgaactg aaggaaaaag aagaattcct gaagtacgcc   2220
gactctgggg cattcacggg ggtttccggc tatctgtatt ttctgcagca tgcgggaacg   2280
gttcagaaaa aaacgaatg gatcgaactc atacatgaag ctctgccagt ccttgaagct   2340
gtcatcgaac aagacgaaaa ctgcgatatc atcagcggtt ctgccggtgc tctaatggtt   2400
ctgatgtcat tgtatgaaca actgatgac ccggtttttc taaagctcgc cgaaaagtgc   2460
gccggccatt tgcttcagca taaaacaaat attgaaaacg gagcggcctg gaaagatcct   2520
catacacaaa actattacac aggatttgcc cacggcactt ccggcatcgc cgcagcttta   2580
tcccgattca ataaagtgtt tgattcgcaa tcactgaaaa aaatcatttc gcaatgcctg   2640
gcatttgaaa agcagctgta catcgcttcc gaaaaaaatt ggggatcaaa aggaagagaa   2700
caactgtcag ttgcatggtg ccatggcgct gccggcatat tgttgtcgag aagcatcctc   2760
cgagaaaacg gagtcaatga tcccgggctg cataccgaca tcttgaacgc tcttgaaaca   2820
actgttaagc atgggctcgg caataaccgc tcattctgtc acggcgattt cggccaactc   2880
gaaatcctaa gagggttcag ggaagaattc agcgaactga acaccattat acagaatacg   2940
gaagatcggc tgttgacata ttttcaagaa aatccattca gtaaaggggt atcacgaggt   3000
gtggattcag ccgggctcat gcttggttta agcggagtcg ctacggcat gctgcaatgc    3060
caatatggag aagaactgcc ggaactgctt cagctcagtc cgcctcaagc gcttatcaaa   3120
aagaacagca aagcttttaa aagagaaaac gtgttttaa                          3159
```

<210> SEQ ID NO 19
<211> LENGTH: 3081
<212> TYPE: DNA
<213> ORGANISM: Bacillus licheniformis

<400> SEQUENCE: 19

| | | | | | | |
|---|---|---|---|---|---|---|
| atgagcatga | aagaattcga | aatttatctg | tataaagctc | tttacagcaa | tgaacgaggc | 60 |
| ggtcaaggtc | aagaacatcc | gtccggcttt | tttccggaaa | acggaaaaac | tccgtctcgt | 120 |
| cctacggatt | ttcacctttc | ttctgtccaa | cattcaccca | atgagcctgt | gcagctgcaa | 180 |
| ggcaaaatgc | cggaatgggc | tgcctgtttg | tctgaaatta | tgaaatacaa | ccctaaagcg | 240 |
| gtttccgaat | aaaacaccc | gcttccccac | atgtcatttg | tcaccttctt | ggttcctttt | 300 |
| cttttatttg | cacaagaacg | gatgtcgaaa | gcttttttctg | aatttgagaa | gcaggaaggc | 360 |
| ggtctatccg | gcataatcga | cgctgccggc | tatcaagacg | gcatcatgtc | tgaacttcac | 420 |
| caatgccttg | ataagctggc | gacgagaaca | cttatcacag | agctgaatgt | agcccgggaa | 480 |
| gacggccggc | taaggggggc | gtcaccggaa | gagcgatatg | tttactttgt | tgaacaatac | 540 |
| atttccgatc | ctgaaattta | ccgggaattt | ttcgagcttt | accctgtgct | tggcaggctg | 600 |
| atggctgaga | aggttctcag | ggtgctcgag | attcatgaag | aaattattgg | gagattttta | 660 |
| agcgaccgca | gcctgattgc | gaaaaaattt | aatatcgctt | cccccgaatt | ggttggattt | 720 |
| gaagggatt | tgggagattc | ccacaaaaac | gggcagagtc | aaagtgct | ggtgttaaac | 780 |
| aacggaaagc | tcgtgtataa | accgcggtcc | ttgtcaattg | acgaacatta | cagggagctg | 840 |
| ctgaactggc | tgaacggacg | gggaatgaag | tacagcctcc | gtgctgcgga | agtgcttgac | 900 |
| aggggaaatt | acggctggca | ggaatttgta | aagcatgaag | gctgttcttc | agaagaagaa | 960 |
| ctggaaagat | tttatttccg | gcagggcgga | catttggcga | tattgtacgg | attgcgctcc | 1020 |
| gtcgattttc | ataatgaaaa | tatcatcgcc | tcaggcgaac | accccatcct | gattgatctg | 1080 |
| gagactcttt | tgacaacca | tgtcagcatt | ttcgctcaaa | atcaaaacct | ccatgtcacc | 1140 |
| gcattggagc | tgaagcattc | cgtgctgtct | tcgatgatgc | ttccggtcaa | attcaaacat | 1200 |
| gatgaagtgc | tcgattttga | tttaagcggg | atcggcggca | aaggcggcca | gcagtcaaag | 1260 |
| aaagcgaagg | gctacgccgt | cctgaattac | ggtgaggaca | ggatgtcttt | aaaagaaaca | 1320 |
| tcgctgacca | ccgaggaaaa | attgaatgcg | cccaaactaa | atggacgtcc | ggtgtccgcc | 1380 |
| gttttctata | cggactttat | cgtggaagga | tttaaaaatg | cttatgccat | tatgatgaaa | 1440 |
| cataaagaag | aactggcagg | accctcgggg | ttttttgaatc | tgtttaagca | cgacgaagtc | 1500 |
| cgccacgtct | tccggccgac | acatgtgtac | ggcaagtttc | tcgaagcgag | cacccaccct | 1560 |
| gactacttga | ccgccggaga | taaacgagag | caattatttg | attatatgtg | gatgctcgcc | 1620 |
| aaacagtcgg | aaaaggcaaa | cgtgtttatt | ccggacgaaa | ttgtcgatct | gctgcttcat | 1680 |
| gatattccct | actttacttt | ttatgctggg | ggcacttccc | tgctcaattc | aagaggggaa | 1740 |
| gaatcggaag | gttttttatga | aacatcaagt | attgatttgg | caaagaaaaa | aattcaatct | 1800 |
| ttctcggaaa | aggatttgaa | tcatcagctc | cgctatattt | ctttatcaat | ggcgacgttg | 1860 |
| attgaaaatg | tctgggacca | tgcagaaagc | gggcttggac | agaaggaaac | ggtcgctgat | 1920 |
| ctcggaaaag | aggtcaagca | tatagctgat | gatttgctgc | agaaggcgat | ctattcagag | 1980 |
| cgcggtgaag | gtcctttctg | gatcagcaat | aatgccggaa | acgaaaaaat | ggtgtttttg | 2040 |
| tcgccgcttc | ctatggggct | ttacgacgga | atggcagggc | tggcaatatt | ttttgcacaa | 2100 |
| gcaggcaagg | tactgaacga | gcaggtatat | acggatacgg | caagatcaat | gatagaagaa | 2160 |
| attcaaaagg | aagaaagtta | ttgggttcaa | aatgggaatt | cccattctgc | tttttttcggc | 2220 |

```
acaggctcat tcatttacct gtattcctat cttggcagtc tatgggaaga cgattcctta    2280
ttggaaaggg cgttgaacct cattccccga gttttggatc agccgaatca acacaaaac    2340 ccggattta tcgcagggga ttcaggattg ctgacagtgc ttgttaatct gtacgaaatc    2400
aagcagcacc cagcagtatt ggactctata agacaggtac tgagcagatt gaatgatcga    2460
attggccgct tacttgattc aatcgagcag gatgccgttt cgttgacggg attttcacac    2520
ggcttgacgg ggatcgcatt ttctatcgca aaggcggcga aggtgataca cgatgacagc    2580
tgcaaagagc ttgtcctaaa gcttgtcgaa gaagaggacc gctattttca aaggatcat    2640 ctaaactggc tagattacg aaatgattcg catacgctgt ccccaagcta ctggtgtcat    2700
ggagctcccg ggattttgct ggggagagcg cacattcagg cttttattcc tgaattgact    2760
acccggactt taaagcttca agaagcgctt caaagttctt taaatctagc agactgtcaa    2820
aatcattcgc tgtgccacgg tttaattggg aatttgaaca ttctgctgga tatcaaaagg    2880
ctgaaccggg aacttcatgt ccctgatgat atattttgca tttataaaac gaaaaaccgg    2940
ggatggaaaa cgggtttgca ttccgatgtg aatcgcttg gcatgtttgt cgggacggca    3000
ggaatagcct acgggctttt gcggctcctc gatgaatctg ttccatccgt attaactctc    3060
gatattccga cgggcaggtg a                                              3081
```

<210> SEQ ID NO 20
<211> LENGTH: 1059
<212> TYPE: PRT
<213> ORGANISM: Bacillus halodurans

<400> SEQUENCE: 20

```
Met Arg Glu Leu Gln Asn Ala Leu Tyr Phe Ser Glu Val Val Phe Gly
1               5                   10                  15

Pro Asn Leu Glu Lys Ile Val Gly Glu Lys Arg Leu Asn Phe Trp Leu
                20                  25                  30

Lys Leu Ile Gly Glu Asp Pro Glu Asn Leu Lys Glu Phe Leu Ser Arg
            35                  40                  45

Lys Gly Asn Ser Phe Glu Glu Gln Thr Leu Pro Glu Lys Glu Ala Ile
        50                  55                  60

Val Pro Asn Arg Leu Gly Glu Ala Leu Glu Lys Val Arg Glu Glu
65                  70                  75                  80

Leu Glu Phe Leu Asn Thr Tyr Ser Thr Lys His Val Arg Arg Val Lys
                85                  90                  95

Glu Leu Gly Val Gln Ile Pro Phe Glu Gly Ile Leu Leu Pro Phe Ile
            100                 105                 110

Ser Met Tyr Ile Glu Lys Phe Gln Gln Gln Leu Arg Lys Lys Ile
        115                 120                 125

Gly Pro Ile His Glu Glu Ile Trp Thr Gln Ile Val Gln Asp Ile Thr
    130                 135                 140

Ser Lys Leu Asn Ala Ile Leu His Arg Thr Leu Ile Leu Glu Leu Asn
145                 150                 155                 160

Val Ala Arg Val Thr Ser Gln Leu Lys Gly Asp Thr Pro Glu Glu Arg
                165                 170                 175

Phe Ala Tyr Tyr Ser Lys Thr Tyr Leu Gly Lys Arg Glu Val Thr His
            180                 185                 190

Arg Leu Tyr Ser Glu Tyr Pro Val Val Leu Arg Leu Phe Thr Thr
        195                 200                 205

Ile Ser His His Ile Ser Phe Ile Thr Glu Ile Leu Glu Arg Val Ala
    210                 215                 220
```

-continued

```
Asn Asp Arg Glu Ala Ile Glu Thr Glu Phe Ser Pro Cys Ser Pro Ile
225                 230                 235                 240

Gly Thr Leu Ala Ser Leu His Leu Asn Ser Gly Asp Ala His His Lys
            245                 250                 255

Gln Arg Thr Val Thr Ile Leu Glu Phe Ser Ser Ser Leu Lys Leu Val
        260                 265                 270

Tyr Lys Pro Arg Ser Leu Lys Val Asp Gly Val Phe Asn Gly Leu Leu
    275                 280                 285

Ala Phe Leu Asn Asp Arg Thr Gly Glu Val Ile Lys Asp Gln Tyr Cys
290                 295                 300

Pro Lys Val Leu Gln Arg Asp Gly Tyr Gly Tyr Val Glu Phe Val Thr
305                 310                 315                 320

His Gln Ser Cys Gln Ser Leu Glu Glu Val Ser Asp Phe Tyr Glu Arg
                325                 330                 335

Leu Gly Ser Leu Met Ser Leu Ser Tyr Val Leu Asn Ser Ser Asp Phe
            340                 345                 350

His Phe Glu Asn Ile Ile Ala His Gly Pro Tyr Pro Val Leu Ile Asp
        355                 360                 365

Leu Glu Thr Ile Ile His Asn Thr Ala Asp Ser Ser Glu Glu Thr Ser
370                 375                 380

Thr Ala Met Asp Arg Ala Phe Arg Met Leu Asn Asp Ser Val Leu Ser
385                 390                 395                 400

Thr Gly Met Leu Pro Ser Ser Ile Tyr Tyr Arg Asp Gln Pro Asn Met
                405                 410                 415

Lys Gly Leu Asn Val Gly Gly Val Ser Lys Ser Glu Gly Gln Lys Thr
            420                 425                 430

Pro Phe Lys Val Asn Gln Ile Ala Asn Arg Asn Thr Asp Glu Met Arg
        435                 440                 445

Ile Glu Lys Asp His Val Thr Leu Ser Ser Gln Lys Asn Leu Pro Ile
450                 455                 460

Phe Gln Ser Ala Ala Met Glu Ser Val His Phe Leu Asp Gln Ile Gln
465                 470                 475                 480

Lys Gly Phe Thr Ser Met Tyr Gln Trp Ile Glu Lys Asn Lys Gln Glu
                485                 490                 495

Phe Lys Glu Gln Val Arg Lys Phe Glu Gly Val Pro Val Arg Ala Val
            500                 505                 510

Leu Arg Ser Thr Thr Arg Tyr Thr Glu Leu Leu Lys Ser Ser Tyr His
        515                 520                 525

Pro Asp Leu Leu Arg Ser Ala Leu Asp Arg Glu Val Leu Leu Asn Arg
530                 535                 540

Leu Thr Val Asp Ser Val Met Thr Pro Tyr Leu Lys Glu Ile Ile Pro
545                 550                 555                 560

Leu Glu Val Glu Asp Leu Leu Asn Gly Asp Val Pro Tyr Phe Tyr Thr
                565                 570                 575

Leu Pro Glu Glu Arg Ala Leu Tyr Gln Glu Ala Ser Ala Ile Asn Ser
            580                 585                 590

Thr Phe Phe Thr Thr Ser Ile Phe His Lys Ile Asp Gln Lys Ile Asp
        595                 600                 605

Lys Leu Gly Ile Glu Asp His Thr Gln Met Lys Ile Leu His Met
610                 615                 620

Ser Met Leu Ala Ser Asn Ala Asn His Tyr Ala Asp Val Ala Asp Leu
625                 630                 635                 640

Asp Ile Gln Lys Gly His Thr Ile Lys Asn Glu Gln Tyr Val Glu Met
                645                 650                 655
```

```
Ala Lys Asp Ile Gly Asp Tyr Leu Met Glu Leu Ser Val Glu Gly Glu
            660                 665                 670

Asn Gln Gly Glu Pro Asp Leu Cys Trp Ile Ser Thr Val Leu Glu Gly
            675                 680                 685

Ser Ser Glu Ile Ile Trp Asp Ile Ser Pro Val Gly Glu Asp Leu Tyr
690                 695                 700

Asn Gly Ser Ala Gly Val Ala Leu Phe Tyr Ala Tyr Leu Phe Lys Ile
705                 710                 715                 720

Thr Gly Glu Lys Arg Tyr Gln Glu Ile Ala Tyr Lys Ala Leu Val Pro
            725                 730                 735

Val Arg Arg Ser Val Ala Gln Phe Gln His His Pro Asn Trp Ser Ile
            740                 745                 750

Gly Ala Phe Asn Gly Ala Ser Gly Tyr Leu Tyr Ala Met Gly Thr Ile
            755                 760                 765

Ala Ala Leu Phe Asn Asp Glu Arg Leu Lys His Glu Val Thr Arg Ser
770                 775                 780

Ile Pro His Ile Glu Pro Met Ile His Glu Asp Lys Ile Tyr Asp Phe
785                 790                 795                 800

Ile Gly Gly Ser Ala Gly Ala Leu Lys Val Phe Leu Ser Leu Ser Gly
            805                 810                 815

Leu Phe Asp Glu Pro Lys Phe Leu Glu Leu Ala Ile Ala Cys Ser Glu
            820                 825                 830

His Leu Met Lys Asn Ala Ile Lys Thr Asp Gln Gly Ile Gly Trp Lys
            835                 840                 845

Pro Pro Trp Glu Val Thr Pro Leu Thr Gly Phe Ser His Gly Val Ser
850                 855                 860

Gly Val Met Ala Ser Phe Ile Glu Leu Tyr Gln Gln Thr Gly Asp Glu
865                 870                 875                 880

Arg Leu Leu Ser Tyr Ile Asp Gln Ser Leu Ala Tyr Glu Arg Ser Phe
            885                 890                 895

Phe Ser Glu Gln Glu Glu Asn Trp Leu Thr Pro Asn Lys Glu Thr Pro
            900                 905                 910

Val Val Ala Trp Cys His Gly Ala Pro Gly Ile Leu Val Ser Arg Leu
            915                 920                 925

Leu Leu Lys Lys Cys Gly Tyr Leu Asp Glu Lys Val Glu Lys Glu Ile
            930                 935                 940

Glu Val Ala Leu Ser Thr Thr Ile Arg Lys Gly Leu Gly Asn Asn Arg
945                 950                 955                 960

Ser Leu Cys His Gly Asp Phe Gly Gln Leu Gly Ile Leu Arg Phe Ala
            965                 970                 975

Ala Glu Val Leu Gly Asp Ser Tyr Leu Gln Glu Val Val Asn Asn Leu
            980                 985                 990

Ser Gly Glu Leu Tyr Asn Leu Phe Lys Thr Glu Gly Tyr Gln Ser Gly
            995                1000                1005

Thr Ser Arg Gly Thr Glu Ser Val Gly Leu Met Val Gly Leu Ser
            1010                1015                1020

Gly Phe Gly Tyr Gly Leu Leu Ser Ala Ala Tyr Pro Ser Ala Val
            1025                1030                1035

Pro Ser Ile Leu Thr Leu Asp Gly Glu Ile Gln Lys Tyr Arg Glu
            1040                1045                1050

Pro His Glu Ala Asn His
            1055
```

-continued

```
<210> SEQ ID NO 21
<211> LENGTH: 988
<212> TYPE: PRT
<213> ORGANISM: Bacillus halodurans

<400> SEQUENCE: 21

Thr Pro Leu Thr Ser Glu His Pro Ser Val Pro Thr Thr Leu Pro His
1               5                   10                  15

Thr Asn Asp Thr Asp Trp Leu Glu Gln Leu His Asp Ile Leu Ser Ile
            20                  25                  30

Pro Val Thr Glu Glu Ile Gln Lys Tyr Phe His Ala Glu Asn Asp Leu
        35                  40                  45

Phe Ser Phe Phe Tyr Thr Pro Phe Leu Gln Phe Thr Tyr Gln Ser Met
    50                  55                  60

Ser Asp Tyr Phe Met Thr Phe Lys Thr Asp Met Ala Leu Ile Glu Arg
65                  70                  75                  80

Gln Ser Leu Leu Gln Ser Thr Leu Thr Ala Val His His Arg Leu Phe
                85                  90                  95

His Leu Thr His Arg Thr Leu Ile Ser Glu Met His Ile Asp Lys Leu
            100                 105                 110

Thr Val Gly Leu Asn Gly Ser Thr Pro His Glu Arg Tyr Met Asp Phe
        115                 120                 125

Asn His Lys Phe Asn Lys Thr Ser Lys Ser Lys Asn Leu Phe Asn Ile
    130                 135                 140

Tyr Pro Ile Leu Gly Lys Leu Val Val Asn Glu Thr Leu Arg Thr Ile
145                 150                 155                 160

Asn Phe Val Lys Lys Ile Ile Gln His Tyr Met Lys Asp Tyr Leu Leu
                165                 170                 175

Leu Ser Asp Phe Phe Lys Glu Lys Asp Leu Arg Leu Thr Asn Leu Gln
            180                 185                 190

Leu Gly Val Gly Asp Thr His Val Asn Gly Gln Cys Val Thr Ile Leu
        195                 200                 205

Thr Phe Ala Ser Gly Gln Lys Val Val Tyr Lys Pro Arg Ser Leu Ser
    210                 215                 220

Ile Asp Lys Gln Phe Gly Glu Phe Ile Glu Trp Val Asn Ser Lys Gly
225                 230                 235                 240

Phe Gln Pro Ser Leu Arg Ile Pro Ile Ala Ile Asp Arg Gln Thr Tyr
                245                 250                 255

Gly Trp Tyr Glu Phe Ile Pro His Gln Glu Ala Thr Ser Glu Asp Glu
            260                 265                 270

Ile Glu Arg Tyr Tyr Ser Arg Ile Gly Gly Tyr Leu Ala Ile Ala Tyr
        275                 280                 285

Leu Phe Gly Ala Thr Asp Leu His Leu Asp Asn Leu Ile Ala Cys Gly
    290                 295                 300

Glu His Pro Met Leu Ile Asp Leu Glu Thr Leu Phe Thr Asn Asp Leu
305                 310                 315                 320

Asp Cys Tyr Asp Ser Ala Phe Pro Phe Pro Ala Leu Ala Arg Glu Leu
                325                 330                 335

Thr Gln Ser Val Phe Gly Thr Leu Met Leu Pro Ile Thr Ile Ala Ser
            340                 345                 350

Gly Lys Leu Leu Asp Ile Asp Leu Ser Ala Val Gly Gly Gly Lys Gly
        355                 360                 365

Val Gln Ser Glu Lys Ile Lys Thr Trp Val Ile Val Asn Gln Lys Thr
    370                 375                 380
```

```
Asp Glu Met Lys Leu Val Glu Gln Pro Tyr Val Thr Glu Ser Ser Gln
385                 390                 395                 400

Asn Lys Pro Thr Val Asn Gly Lys Glu Ala Asn Ile Gly Asn Tyr Ile
            405                 410                 415

Pro His Val Thr Asp Gly Phe Arg Lys Met Tyr Arg Leu Phe Leu Asn
        420                 425                 430

Glu Ile Asp Glu Leu Met Asp His Asn Gly Pro Ile Phe Ala Phe Glu
    435                 440                 445

Ser Cys Gln Ile Arg His Val Phe Arg Ala Thr His Val Tyr Ala Lys
    450                 455                 460

Phe Leu Glu Ala Ser Thr His Pro Asp Tyr Leu Gln Glu Pro Thr Arg
465                 470                 475                 480

Arg Asn Lys Leu Phe Glu Ser Phe Trp Asn Ile Thr Ser Leu Met Ala
            485                 490                 495

Pro Phe Lys Lys Ile Val Pro His Glu Ile Ala Glu Leu Glu Asn His
        500                 505                 510

Asp Ile Pro Tyr Phe Val Leu Thr Cys Gly Gly Thr Ile Val Lys Asp
    515                 520                 525

Gly Tyr Gly Arg Asp Ile Ala Asp Leu Phe Gln Ser Ser Cys Ile Glu
530                 535                 540

Arg Val Thr His Arg Leu Gln Gln Leu Gly Ser Glu Asp Glu Ala Arg
545                 550                 555                 560

Gln Ile Arg Tyr Ile Lys Ser Ser Leu Ala Thr Leu Thr Asn Gly Asp
            565                 570                 575

Trp Thr Pro Ser His Glu Lys Thr Pro Met Ser Pro Ala Ser Ala Asp
        580                 585                 590

Arg Glu Asp Gly Tyr Phe Leu Arg Glu Ala Gln Ala Ile Gly Asp Asp
    595                 600                 605

Ile Leu Ala Gln Leu Ile Trp Glu Asp Asp Arg His Ala Ala Tyr Leu
    610                 615                 620

Ile Gly Val Ser Val Gly Met Asn Glu Ala Val Thr Val Ser Pro Leu
625                 630                 635                 640

Thr Pro Gly Ile Tyr Asp Gly Thr Leu Gly Ile Val Leu Phe Phe Asp
            645                 650                 655

Gln Leu Ala Gln Gln Thr Gly Glu Thr His Tyr Arg His Ala Ala Asp
        660                 665                 670

Ala Leu Leu Glu Gly Met Phe Lys Gln Leu Lys Pro Glu Leu Met Pro
    675                 680                 685

Ser Ser Ala Tyr Phe Gly Leu Gly Ser Leu Phe Tyr Gly Leu Met Val
    690                 695                 700

Leu Gly Leu Gln Arg Ser Asp Ser His Ile Ile Gln Lys Ala Tyr Glu
705                 710                 715                 720

Tyr Leu Lys His Leu Glu Glu Cys Val Gln His Glu Glu Thr Pro Asp
            725                 730                 735

Phe Val Ser Gly Leu Ser Gly Val Leu Tyr Met Leu Thr Lys Ile Tyr
        740                 745                 750

Gln Leu Thr Asn Glu Pro Arg Val Phe Glu Val Ala Lys Thr Thr Ala
    755                 760                 765

Ser Arg Leu Ser Val Leu Leu Asp Ser Lys Gln Pro Asp Thr Val Leu
    770                 775                 780

Thr Gly Leu Ser His Gly Ala Ala Gly Phe Ala Leu Ala Leu Leu Thr
785                 790                 795                 800

Tyr Gly Thr Ala Ala Asn Asp Glu Gln Leu Leu Lys Gln Gly His Ser
            805                 810                 815
```

```
Tyr Leu Val Tyr Glu Arg Asn Arg Phe Asn Lys Gln Glu Asn Asn Trp
                820                 825                 830

Val Asp Leu Arg Lys Gly Asn Ala Tyr Gln Thr Phe Trp Cys His Gly
            835                 840                 845

Ala Pro Gly Ile Gly Ile Ser Arg Leu Leu Ala Gln Phe Tyr Asp
        850                 855                 860

Asp Glu Leu Leu His Glu Leu Asn Ala Ala Leu Asn Lys Thr Ile
865                 870                 875                 880

Ser Asp Gly Phe Gly His Asn His Ser Leu Cys His Gly Asp Phe Gly
                885                 890                 895

Asn Leu Asp Leu Leu Leu Tyr Ala Gln Tyr Thr Asn Asn Pro Glu
            900                 905                 910

Pro Lys Glu Leu Ala Arg Lys Leu Ala Ile Ser Ser Ile Asp Gln Ala
                915                 920                 925

His Thr Tyr Gly Trp Lys Leu Gly Leu Asn His Ser Asp Gln Leu Gln
            930                 935                 940

Gly Met Met Leu Gly Val Thr Gly Ile Gly Tyr Gln Leu Leu Arg His
945                 950                 955                 960

Ile Asn Pro Thr Val Pro Ser Ile Leu Ala Leu Glu Leu Pro Ser Ser
                965                 970                 975

Thr Leu Thr Glu Lys Glu Leu Arg Ile His Asp Arg
            980                 985

<210> SEQ ID NO 22
<211> LENGTH: 1052
<212> TYPE: PRT
<213> ORGANISM: Bacillus licheniformis

<400> SEQUENCE: 22

Met Asn Glu Lys Ser Ala Gly Tyr His Glu Arg Leu Pro Val Ala Gln
1               5                   10                  15

Thr Gln Ser Pro Leu Val Asn Asp Lys Ile Lys Tyr Trp Arg Ser Leu
            20                  25                  30

Phe Gly Asp Asp Lys Trp Leu Asn Lys Ala Val Ser Leu Leu Ser
        35                  40                  45

His Asp Pro Leu Ser Ser Ile Ala Gln Ser Val Ser Gln Ser Val
    50                  55                  60

Gly Leu Lys Asp Ser Arg Arg Gly Pro Trp Gln Lys Met Gln Lys Arg
65                  70                  75                  80

Ile Phe Glu Thr Pro Phe Ser Tyr Lys Asp Ser Ala Leu Gln Asp Ser
                85                  90                  95

Glu Leu Leu Phe Asp Ser Leu Leu Thr Arg Phe Ala Ser Ala Ala Gln
            100                 105                 110

Asp Ala Leu Glu Glu Gln Asn Ile Ile Leu Ser Pro Pro Leu Cys Arg
        115                 120                 125

Gln Val Leu Thr His Leu Lys Gln Thr Leu Leu Gln Ile Ala His Gln
    130                 135                 140

Thr Leu Ile Leu Glu Leu Asn Ile Leu Arg Leu Glu Asp Gln Leu Lys
145                 150                 155                 160

Gly Asp Thr Pro Glu Met Arg Tyr Leu Asp Phe Asn Asp Asn Phe Leu
                165                 170                 175

Val Asn Pro Gly Tyr Leu Arg Thr Leu Phe Asn Glu Tyr Pro Val Leu
            180                 185                 190

Leu Arg Leu Leu Cys Thr Lys Thr Asp Tyr Trp Val Gln Asn Phe Ser
        195                 200                 205
```

-continued

```
Glu Leu Trp Lys Arg Leu Arg Gln Asp Arg Glu Gln Leu Gln Ala Ala
    210                 215                 220

Phe His Ile Ala Gly Asp Pro Val His Ile Glu Leu Gly Val Gly Asp
225                 230                 235                 240

Ser His Asn Lys Gly Lys Met Ala Ala Ile Leu Thr Tyr Ser Asp Gly
                245                 250                 255

Lys Lys Ile Val Tyr Lys Pro Arg Ser His Asp Val Asp Asp Ala Phe
                260                 265                 270

Gln Leu Leu Leu Ser Trp Ile Asn Asp Arg Asn Ser Gly Ser Pro Leu
                275                 280                 285

Lys Thr Leu Arg Leu Ile Asn Lys Lys Arg Tyr Gly Trp Ser Glu Phe
290                 295                 300

Ile Pro His Glu Thr Cys His Thr Lys Lys Glu Leu Glu Gly Tyr Tyr
305                 310                 315                 320

Thr Arg Leu Gly Lys Leu Leu Ala Val Leu Tyr Ser Ile Asp Ala Val
                325                 330                 335

Asp Phe His His Glu Asn Ile Ile Ala Ser Gly Glu His Pro Val Leu
                340                 345                 350

Ile Asp Leu Glu Ser Ile Phe His Gln Tyr Lys Lys Arg Asp Glu Pro
                355                 360                 365

Gly Ser Thr Ala Val Asp Lys Ala Asn Tyr Ile Leu Ser Arg Ser Val
370                 375                 380

Arg Ser Thr Gly Ile Leu Pro Phe Asn Leu Tyr Phe Gly Arg Lys Asn
385                 390                 395                 400

Arg Asp Lys Val Val Asp Ile Ser Gly Met Gly Gly Gln Glu Ala Gln
                405                 410                 415

Glu Ser Pro Phe Gln Ala Leu Gln Ile Lys Gly Phe Phe Arg Asp Asp
                420                 425                 430

Ile Arg Leu Glu His Asp Arg Phe Glu Ile Gly Glu Ala Lys Asn Leu
                435                 440                 445

Pro Thr Leu Asp His Gln His Val Pro Val Ala Asp Tyr Leu His Cys
450                 455                 460

Ile Ile Glu Gly Phe Ser Ala Val Tyr Arg Leu Ile Ser Asp His Gly
465                 470                 475                 480

Glu Ser Tyr Leu Ala Thr Ile Glu His Phe Lys Asn Cys Thr Val Arg
                485                 490                 495

Asn Ile Leu Lys Pro Thr Ala His Tyr Ala Ser Leu Leu Asn Lys Ser
                500                 505                 510

Tyr His Pro Asp Phe Leu Arg Asp Ala Val Asp Arg Glu Val Phe Leu
                515                 520                 525

Cys Arg Val Glu Lys Phe Glu Asp Ala Asp Thr Asp Ile Ala Ala Ala
530                 535                 540

Lys Thr Glu Leu Lys Glu Leu Ile Arg Gly Asp Ile Pro Tyr Phe Leu
545                 550                 555                 560

Ser Lys Pro Ser Asp Thr Tyr Leu Leu Asn Gly Glu Glu Pro Ile
                565                 570                 575

Ala Ala Tyr Phe Glu Thr Pro Ser Phe Thr Arg Val Ile Lys Lys Ile
                580                 585                 590

Ser Ser Phe Ser Asp Gln Asp Leu Lys Glu Gln Ala Asn Val Ile Arg
                595                 600                 605

Met Ser Ile Leu Ala Ala Tyr Asn Ala Arg His Glu Lys Asp Ala Ile
610                 615                 620
```

```
Asp Ile Asp Gln Asn His Pro Ser Pro Arg Ser Gly Ala Leu Gln Pro
625                 630                 635                 640

Leu Ala Ile Ala Glu Lys Ala Ala Asp Asp Leu Ala Glu Lys Arg Ile
            645                 650                 655

Glu Gly Asn Asp Gly Lys Asp Val Thr Trp Ile Ser Thr Val Ile Glu
                660                 665                 670

Gly Val Glu Glu Ile Ser Trp Thr Ile Ser Pro Val Ser Leu Asp Leu
        675                 680                 685

Tyr Asn Gly Asn Ala Gly Ile Gly Leu Phe Met Ser Tyr Leu Ser Arg
    690                 695                 700

Phe Ala Lys Arg Pro Glu Thr Tyr Ser His Ile Thr Glu Gln Cys Val
705                 710                 715                 720

Phe Ala Ile Gln Arg Ala Leu Asn Glu Leu Lys Glu Lys Glu Glu Phe
            725                 730                 735

Leu Lys Tyr Ala Asp Ser Gly Ala Phe Thr Gly Val Ser Gly Tyr Leu
                740                 745                 750

Tyr Phe Leu Gln His Ala Gly Thr Val Gln Lys Lys Asn Glu Trp Ile
        755                 760                 765

Glu Leu Ile His Glu Ala Leu Pro Val Leu Glu Ala Val Ile Glu Gln
    770                 775                 780

Asp Glu Asn Cys Asp Ile Ile Ser Gly Ser Ala Gly Ala Leu Met Val
785                 790                 795                 800

Leu Met Ser Leu Tyr Glu Gln Leu Asp Asp Pro Val Phe Leu Lys Leu
            805                 810                 815

Ala Glu Lys Cys Ala Gly His Leu Leu Gln His Lys Thr Asn Ile Glu
                820                 825                 830

Asn Gly Ala Ala Trp Lys Asp Pro His Thr Gln Asn Tyr Tyr Thr Gly
        835                 840                 845

Phe Ala His Gly Thr Ser Gly Ile Ala Ala Leu Ser Arg Phe Asn
    850                 855                 860

Lys Val Phe Asp Ser Gln Ser Leu Lys Lys Ile Ile Ser Gln Cys Leu
865                 870                 875                 880

Ala Phe Glu Lys Gln Leu Tyr Ile Ala Ser Glu Lys Asn Trp Gly Ser
            885                 890                 895

Lys Gly Arg Glu Gln Leu Ser Val Ala Trp Cys His Gly Ala Ala Gly
                900                 905                 910

Ile Leu Leu Ser Arg Ser Ile Leu Arg Glu Asn Gly Val Asn Asp Pro
        915                 920                 925

Gly Leu His Thr Asp Ile Leu Asn Ala Leu Glu Thr Thr Val Lys His
    930                 935                 940

Gly Leu Gly Asn Asn Arg Ser Phe Cys His Gly Asp Phe Gly Gln Leu
945                 950                 955                 960

Glu Ile Leu Arg Gly Phe Arg Glu Glu Phe Ser Glu Leu Asn Thr Ile
            965                 970                 975

Ile Gln Asn Thr Glu Asp Arg Leu Leu Thr Tyr Phe Gln Glu Asn Pro
                980                 985                 990

Phe Ser Lys Gly Val Ser Arg Gly Val Asp Ser Ala Gly Leu Met Leu
        995                 1000                1005

Gly Leu Ser Gly Val Gly Tyr Gly Met Leu Gln Cys Gln Tyr Gly
        1010                1015                1020

Glu Glu Leu Pro Glu Leu Leu Gln Leu Ser Pro Pro Gln Ala Leu
        1025                1030                1035

Ile Lys Lys Asn Ser Lys Ala Phe Lys Arg Glu Asn Val Phe
        1040                1045                1050
```

<210> SEQ ID NO 23
<211> LENGTH: 1026
<212> TYPE: PRT
<213> ORGANISM: Bacillus licheniformis

<400> SEQUENCE: 23

```
Met Ser Met Lys Glu Phe Glu Ile Tyr Leu Tyr Lys Ala Leu Tyr Ser
1               5                   10                  15

Asn Glu Arg Gly Gly Gln Gly Gln Glu His Pro Ser Gly Phe Phe Pro
            20                  25                  30

Glu Asn Gly Lys Thr Pro Ser Arg Pro Thr Asp Phe His Leu Ser Ser
        35                  40                  45

Val Gln His Ser Pro Asn Glu Pro Val Gln Leu Gln Gly Lys Met Pro
    50                  55                  60

Glu Trp Ala Ala Cys Leu Ser Glu Ile Met Lys Tyr Asn Pro Lys Ala
65                  70                  75                  80

Val Ser Glu Leu Lys His Pro Leu Pro His Met Ser Phe Val Thr Phe
                85                  90                  95

Leu Val Pro Phe Leu Leu Phe Ala Gln Glu Arg Met Ser Lys Ala Phe
            100                 105                 110

Ser Glu Phe Glu Lys Gln Glu Gly Gly Leu Ser Gly Ile Ile Asp Ala
        115                 120                 125

Ala Gly Tyr Gln Asp Gly Ile Met Ser Glu Leu His Gln Cys Leu Asp
    130                 135                 140

Lys Leu Ala Thr Arg Thr Leu Ile Thr Glu Leu Asn Val Ala Arg Glu
145                 150                 155                 160

Asp Gly Arg Leu Lys Gly Ala Ser Pro Glu Glu Arg Tyr Val Tyr Phe
                165                 170                 175

Val Glu Gln Tyr Ile Ser Asp Pro Glu Ile Tyr Arg Glu Phe Phe Glu
            180                 185                 190

Leu Tyr Pro Val Leu Gly Arg Leu Met Ala Glu Lys Val Leu Arg Val
        195                 200                 205

Leu Glu Ile His Glu Glu Ile Ile Gly Arg Phe Leu Ser Asp Arg Ser
    210                 215                 220

Leu Ile Ala Lys Lys Phe Asn Ile Ala Ser Pro Glu Leu Val Gly Phe
225                 230                 235                 240

Glu Gly Asp Leu Gly Asp Ser His Lys Asn Gly Gln Ser Val Lys Val
                245                 250                 255

Leu Val Leu Asn Asn Gly Lys Leu Val Tyr Lys Pro Arg Ser Leu Ser
            260                 265                 270

Ile Asp Glu His Tyr Arg Glu Leu Leu Asn Trp Leu Asn Gly Arg Gly
        275                 280                 285

Met Lys Tyr Ser Leu Arg Ala Ala Glu Val Leu Asp Arg Gly Asn Tyr
    290                 295                 300

Gly Trp Gln Glu Phe Val Lys His Glu Gly Cys Ser Ser Glu Glu Glu
305                 310                 315                 320

Leu Glu Arg Phe Tyr Phe Arg Gln Gly Gly His Leu Ala Ile Leu Tyr
                325                 330                 335

Gly Leu Arg Ser Val Asp Phe His Asn Glu Asn Ile Ile Ala Ser Gly
            340                 345                 350

Glu His Pro Ile Leu Ile Asp Leu Glu Thr Leu Phe Asp Asn His Val
        355                 360                 365

Ser Ile Phe Ala Gln Asn Gln Asn Leu His Val Thr Ala Leu Glu Leu
    370                 375                 380
```

```
Lys His Ser Val Leu Ser Ser Met Met Leu Pro Val Lys Phe Lys His
385                 390                 395                 400

Asp Glu Val Leu Asp Phe Asp Leu Ser Gly Ile Gly Gly Lys Gly Gly
                405                 410                 415

Gln Gln Ser Lys Lys Ala Lys Gly Tyr Ala Val Leu Asn Tyr Gly Glu
            420                 425                 430

Asp Arg Met Ser Leu Lys Glu Thr Ser Leu Thr Thr Glu Glu Lys Leu
        435                 440                 445

Asn Ala Pro Lys Leu Asn Gly Arg Pro Val Ser Ala Val Phe Tyr Thr
450                 455                 460

Asp Phe Ile Val Glu Gly Phe Lys Asn Ala Tyr Ala Ile Met Met Lys
465                 470                 475                 480

His Lys Glu Glu Leu Ala Gly Pro Ser Gly Phe Leu Asn Leu Phe Lys
                485                 490                 495

His Asp Glu Val Arg His Val Phe Arg Pro Thr His Val Tyr Gly Lys
            500                 505                 510

Phe Leu Glu Ala Ser Thr His Pro Asp Tyr Leu Thr Ala Gly Asp Lys
        515                 520                 525

Arg Glu Gln Leu Phe Asp Tyr Met Trp Met Leu Ala Lys Gln Ser Glu
    530                 535                 540

Lys Ala Asn Val Phe Ile Pro Asp Glu Ile Val Asp Leu Leu Leu His
545                 550                 555                 560

Asp Ile Pro Tyr Phe Thr Phe Tyr Ala Gly Gly Thr Ser Leu Leu Asn
                565                 570                 575

Ser Arg Gly Glu Glu Ser Glu Gly Phe Tyr Glu Thr Ser Ser Ile Asp
            580                 585                 590

Leu Ala Lys Lys Lys Ile Gln Ser Phe Ser Lys Asp Leu Asn His
        595                 600                 605

Gln Leu Arg Tyr Ile Ser Leu Ser Met Ala Thr Leu Ile Glu Asn Val
    610                 615                 620

Trp Asp His Ala Glu Ser Gly Leu Gly Gln Lys Glu Thr Val Ala Asp
625                 630                 635                 640

Leu Gly Lys Glu Val Lys His Ile Ala Asp Asp Leu Leu Gln Lys Ala
                645                 650                 655

Ile Tyr Ser Glu Arg Gly Glu Gly Pro Phe Trp Ile Ser Asn Asn Ala
            660                 665                 670

Gly Asp Glu Lys Met Val Phe Leu Ser Pro Leu Pro Met Gly Leu Tyr
        675                 680                 685

Asp Gly Met Ala Gly Leu Ala Ile Phe Phe Ala Gln Ala Gly Lys Val
    690                 695                 700

Leu Asn Glu Gln Val Tyr Thr Asp Thr Ala Arg Ser Met Ile Glu Glu
705                 710                 715                 720

Ile Gln Lys Glu Glu Ser Tyr Trp Val Gln Asn Gly Asn Ser His Ser
                725                 730                 735

Ala Phe Phe Gly Thr Gly Ser Phe Ile Tyr Leu Tyr Ser Tyr Leu Gly
            740                 745                 750

Ser Leu Trp Glu Asp Asp Ser Leu Leu Glu Arg Ala Leu Asn Leu Ile
        755                 760                 765

Pro Arg Val Leu Asp Gln Pro Asn Gln Thr Gln Asn Pro Asp Phe Ile
770                 775                 780

Ala Gly Asp Ser Gly Leu Leu Thr Val Leu Val Asn Leu Tyr Glu Ile
785                 790                 795                 800

Lys Gln His Pro Ala Val Leu Asp Ser Ile Arg Gln Val Leu Ser Arg
                805                 810                 815
```

-continued

```
Leu Asn Asp Arg Ile Gly Arg Leu Leu Asp Ser Ile Glu Gln Asp Ala
            820                 825                 830
Val Ser Leu Thr Gly Phe Ser His Gly Leu Thr Gly Ile Ala Phe Ser
        835                 840                 845
Ile Ala Lys Ala Ala Lys Val Ile His Asp Asp Ser Cys Lys Glu Leu
    850                 855                 860
Val Leu Lys Leu Val Glu Glu Asp Arg Tyr Phe Gln Lys Asp His
865                 870                 875                 880
Leu Asn Trp Leu Asp Leu Arg Asn Asp Ser His Thr Leu Ser Pro Ser
                885                 890                 895
Tyr Trp Cys His Gly Ala Pro Gly Ile Leu Leu Gly Arg Ala His Ile
            900                 905                 910
Gln Ala Phe Ile Pro Glu Leu Thr Thr Arg Thr Leu Lys Leu Gln Glu
        915                 920                 925
Ala Leu Gln Ser Ser Leu Asn Leu Ala Asp Cys Gln Asn His Ser Leu
    930                 935                 940
Cys His Gly Leu Ile Gly Asn Leu Asn Ile Leu Leu Asp Ile Lys Arg
945                 950                 955                 960
Leu Asn Arg Glu Leu His Val Pro Asp Asp Ile Phe Cys Ile Tyr Lys
                965                 970                 975
Thr Lys Asn Arg Gly Trp Lys Thr Gly Leu His Ser Asp Val Glu Ser
            980                 985                 990
Leu Gly Met Phe Val Gly Thr Ala Gly Ile Ala Tyr Gly Leu Leu Arg
        995                1000                1005
Leu Leu Asp Glu Ser Val Pro Ser Val Leu Thr Leu Asp Ile Pro
    1010                1015                1020
Thr Gly Arg
    1025
```

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
gcgccgcata tgacaaatct t                                             21

<210> SEQ ID NO 25
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 25
aggctcgagt tagttgcaag a                                             21

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26
gcgccgcata tggtaaattc a                                             21

```
<210> SEQ ID NO 27
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 27
aaactcgagt tagcactggc t                                              21

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 28
gccgctagca tgagagaatt a                                              21

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 29
cgtctcgagt taatgattcg c                                              21

<210> SEQ ID NO 30
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 30
gggtatccgc tcgagatgaa aactcctcta acaagt                              36

<210> SEQ ID NO 31
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 31
tataaacgcg gatccttatc tgtcatgaat tctcaa                              36

<210> SEQ ID NO 32
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 32
attctagctg ggattgaagg tcgttgcgca tggtac                              36

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide
```

-continued

```
<400> SEQUENCE: 33
aggctcgagt tagttgcaag a                                                   21

<210> SEQ ID NO 34
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 34
gcttcaggag atattgaagg tcgtacaact tggcct                                   36

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 35
aaactcgagt tagcactggc t                                                   21

<210> SEQ ID NO 36
<211> LENGTH: 4
<212> TYPE: PRT
<213> ORGANISM: Artificial sequence
<220> FEATURE:
<223> OTHER INFORMATION: Synthetic peptide

<400> SEQUENCE: 36

Val Asn Gly Ala
1

<210> SEQ ID NO 37
<211> LENGTH: 4
<212> TYPE: PRT
<213> ORGANISM: Artificial sequence
<220> FEATURE:
<223> OTHER INFORMATION: Synthetic peptide

<400> SEQUENCE: 37

Val His Ala Gln
1

<210> SEQ ID NO 38
<211> LENGTH: 41
<212> TYPE: PRT
<213> ORGANISM: Bacillus halodurans

<400> SEQUENCE: 38

Met Thr Asn Leu Leu Lys Glu Trp Lys Met Pro Leu Glu Arg Thr His
1               5                   10                  15

Asn Asn Ser Asn Pro Ala Gly Asp Ile Phe Gln Glu Leu Glu Asp Gln
            20                  25                  30

Asp Ile Leu Ala Gly Val Asn Gly Ala
        35                  40

<210> SEQ ID NO 39
<211> LENGTH: 35
<212> TYPE: PRT
<213> ORGANISM: Bacillus halodurans
```

```
<400> SEQUENCE: 39

Met Val Asn Ser Lys Asp Leu Arg Asn Pro Glu Phe Arg Lys Ala Gln
1               5                   10                  15

Gly Leu Gln Phe Val Asp Glu Val Asn Glu Lys Glu Leu Ser Ser Leu
                20                  25                  30

Ala Gly Ser
        35

<210> SEQ ID NO 40
<211> LENGTH: 4
<212> TYPE: PRT
<213> ORGANISM: Artificial sequence
<220> FEATURE:
<223> OTHER INFORMATION: Synthetic peptide

<400> SEQUENCE: 40

Ala Trp Pro Ser
1

<210> SEQ ID NO 41
<211> LENGTH: 59
<212> TYPE: PRT
<213> ORGANISM: Lactobacillus plantarum

<400> SEQUENCE: 41

Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala Lys Cys
                20                  25                  30

Lys Trp Trp Asn Ile Ser Cys Asp Leu Gly Asn Gly His Val Cys
                35                  40                  45

Thr Leu Ser His Glu Cys Gln Val Ser Cys Asn
        50                  55

<210> SEQ ID NO 42
<211> LENGTH: 62
<212> TYPE: PRT
<213> ORGANISM: Bacillus licheniformis

<400> SEQUENCE: 42

Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Ile Phe Gly Ala
                20                  25                  30

Cys Ser Thr Asn Thr Phe Ser Leu Ser Asp Tyr Trp Gly Asn Lys Gly
                35                  40                  45

Asn Trp Cys Thr Ala Thr His Glu Cys Met Ser Trp Cys Lys
        50                  55                  60

<210> SEQ ID NO 43
<211> LENGTH: 59
<212> TYPE: PRT
<213> ORGANISM: Lactococcus lactis

<400> SEQUENCE: 43

Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
                20                  25                  30
```

-continued

```
Asn Thr Phe Ser Leu Ser Asp Tyr Trp Gly Asn Asn Gly Ala Trp Cys
            35                  40                  45

Thr Leu Thr His Glu Cys Met Ala Trp Cys Lys
    50                  55
```

<210> SEQ ID NO 44
<211> LENGTH: 61
<212> TYPE: PRT
<213> ORGANISM: Streptococcus ratti

<400> SEQUENCE: 44

```
Met Lys Glu Ile Gln Lys Ala Gly Leu Gln Glu Leu Ser Ile Leu
1               5                   10                  15

Met Asp Asp Ala Asn Asn Leu Glu Gln Leu Thr Ala Gly Ile Gly Thr
            20                  25                  30

Thr Val Val Asn Ser Thr Phe Ser Ile Val Leu Gly Asn Lys Gly Tyr
            35                  40                  45

Ile Cys Thr Val Thr Val Glu Cys Met Arg Asn Cys Gln
            50                  55                  60
```

<210> SEQ ID NO 45
<211> LENGTH: 62
<212> TYPE: PRT
<213> ORGANISM: Streptococcus mutans

<400> SEQUENCE: 45

```
Met Lys Glu Ile Gln Lys Ala Gly Leu Gln Glu Leu Ser Ile Leu
1               5                   10                  15

Met Asp Asp Ala Asn Asn Leu Glu Gln Leu Thr Ala Gly Ile Gly Thr
            20                  25                  30

Thr Val Val Asn Ser Thr Phe Ser Ile Val Leu Gly Asn Lys Gly Tyr
            35                  40                  45

Ile Cys Thr Val Thr Val Glu Cys Met Arg Asn Cys Ser Lys
            50                  55                  60
```

<210> SEQ ID NO 46
<211> LENGTH: 67
<212> TYPE: PRT
<213> ORGANISM: Lactobacillus plantarum

<400> SEQUENCE: 46

```
Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
            35                  40                  45

Ser Ile Ala Val Cys Pro Thr Thr Lys Cys Ser Lys Arg Cys Gly Lys
    50                  55                  60

Arg Lys Lys
65
```

<210> SEQ ID NO 47
<211> LENGTH: 62
<212> TYPE: PRT
<213> ORGANISM: Streptococcus ratti -continued

<400> SEQUENCE: 47

Met Lys Ser Asn Leu Leu Lys Ile Asn Asn Val Thr Glu Val Glu Lys
1               5                   10                  15

Asp Met Val Thr Leu Ile Lys Asp Glu Asp Met Glu Leu Ala Gly Gly
            20                  25                  30

Ser Thr Pro Ala Cys Ala Ile Gly Val Val Gly Ile Thr Val Ala Val
        35                  40                  45

Thr Gly Ile Ser Thr Ala Cys Thr Ser Arg Cys Ile Asn Lys
    50                  55                  60

<210> SEQ ID NO 48
<211> LENGTH: 61
<212> TYPE: PRT
<213> ORGANISM: Streptococcus mutans

<400> SEQUENCE: 48

Met Lys Ser Asn Leu Leu Lys Ile Asn Asn Val Thr Glu Met Glu Lys
1               5                   10                  15

Asn Met Val Thr Leu Ile Lys Asp Glu Asp Met Leu Ala Gly Gly Ser
            20                  25                  30

Thr Pro Ala Cys Ala Ile Gly Val Val Gly Ile Thr Val Ala Val Thr
        35                  40                  45

Gly Ile Ser Thr Ala Cys Thr Ser Arg Cys Ile Asn Lys
    50                  55                  60

<210> SEQ ID NO 49
<211> LENGTH: 65
<212> TYPE: PRT
<213> ORGANISM: Lactococcus lactis

<400> SEQUENCE: 49

Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly Thr Thr Pro Ala Thr Pro Ala Ile Ser Ile Leu Ser
        35                  40                  45

Ala Tyr Ile Ser Thr Asn Thr Cys Pro Thr Thr Lys Cys Thr Arg Ala
    50                  55                  60

Cys
65

<210> SEQ ID NO 50
<211> LENGTH: 67
<212> TYPE: PRT
<213> ORGANISM: Bacillus licheniformis

<400> SEQUENCE: 50

Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala Gly Thr Pro Leu Ala Leu Leu Gly Gly Ala Ala Thr Gly
        35                  40                  45

Val Ile Gly Tyr Ile Ser Asn Gln Thr Cys Pro Thr Thr Ala Cys Thr
    50                  55                  60

Arg Ala Cys
65

```
<210> SEQ ID NO 51
<211> LENGTH: 63
<212> TYPE: PRT
<213> ORGANISM: Enterococcus faecalis

<400> SEQUENCE: 51

Met Leu Asn Lys Glu Asn Gln Glu Asn Tyr Tyr Ser Asn Lys Leu Glu
1               5                   10                  15

Leu Val Gly Pro Ser Phe Glu Glu Leu Ser Leu Glu Glu Met Glu Ala
            20                  25                  30

Ile Gln Gly Ser Gly Asp Val Gln Ala Glu Thr Thr Pro Ala Cys Phe
        35                  40                  45

Thr Ile Gly Leu Gly Val Gly Ala Leu Phe Ser Ala Lys Phe Cys
    50                  55                  60

<210> SEQ ID NO 52
<211> LENGTH: 68
<212> TYPE: PRT
<213> ORGANISM: Enterococcus faecalis

<400> SEQUENCE: 52

Met Glu Asn Leu Ser Val Val Pro Ser Phe Glu Glu Leu Ser Val Glu
1               5                   10                  15

Glu Met Glu Ala Ile Gln Gly Ser Gly Asp Val Gln Ala Glu Thr Thr
            20                  25                  30

Pro Val Cys Ala Val Ala Ala Thr Ala Ala Ala Ser Ser Ala Ala Cys
        35                  40                  45

Gly Trp Val Gly Gly Gly Ile Phe Thr Gly Val Thr Val Val Val Ser
    50                  55                  60

Leu Lys His Cys
65

<210> SEQ ID NO 53
<211> LENGTH: 29
<212> TYPE: PRT
<213> ORGANISM: Lactobacillus plantarum
<220> FEATURE:
<221> NAME/KEY: MOD_RES
<222> LOCATION: (19)..(19)
<223> OTHER INFORMATION: Abu

<400> SEQUENCE: 53

Lys Cys Lys Trp Trp Asn Ile Ala Cys Asp Leu Gly Asn Asn Gly His
1               5                   10                  15

Val Ala Xaa Leu Ala His Glu Ala Gln Val Ser Ala Asn
            20                  25

<210> SEQ ID NO 54
<211> LENGTH: 28
<212> TYPE: PRT
<213> ORGANISM: Lactococcus lactis
<220> FEATURE:
<221> NAME/KEY: MOD_RES
<222> LOCATION: (1)..(1)
<223> OTHER INFORMATION: Dehydrobutyrine
<220> FEATURE:
<221> NAME/KEY: MOD_RES
<222> LOCATION: (4)..(4)
<223> OTHER INFORMATION: Dehydrobutyrine
<220> FEATURE:
<221> NAME/KEY: MOD_RES
<222> LOCATION: (8)..(8)
<223> OTHER INFORMATION: D-Alanine
```

```
<220> FEATURE:
<221> NAME/KEY: MOD_RES
<222> LOCATION: (11)..(11)
<223> OTHER INFORMATION: D-Alanine
<220> FEATURE:
<221> NAME/KEY: MOD_RES
<222> LOCATION: (21)..(21)
<223> OTHER INFORMATION: Abu
<220> FEATURE:
<221> NAME/KEY: MOD_RES
<222> LOCATION: (25)..(25)
<223> OTHER INFORMATION: Abu

<400> SEQUENCE: 54

Xaa Pro Ala Xaa Pro Ala Ile Xaa Ile Leu Xaa Ala Tyr Ile Ala Thr
1               5                   10                  15

Asn Thr Ala Pro Xaa Thr Lys Ala Xaa Arg Ala Ala
            20                  25
```